US012760291B2

(12) United States Patent
Tschollar et al.

(10) Patent No.: US 12,760,291 B2
(45) Date of Patent: Oct. 13, 2026

(54) DIPEPTIDYLPEPTIDASE AND LEUCINE AMINOPEPTIDASE POLYPEPTIDE VARIANTS

(71) Applicant: AMYRA BIOTECH AG, Basel (CH)

(72) Inventors: Werner Tschollar, Preverenges (CH); Silvia Tietz, Bern (CH)

(73) Assignee: AMYRA BIOTECH A G, Basel (CH)

( * ) Notice: Subject to any disclaimer, the term of this patent is extended or adjusted under 35 U.S.C. 154(b) by 499 days.

(21) Appl. No.: 18/033,912

(22) PCT Filed: Oct. 25, 2021

(86) PCT No.: PCT/EP2021/079522

§ 371 (c)(1),
(2) Date: Apr. 26, 2023

(87) PCT Pub. No.: WO2022/090144

PCT Pub. Date: May 5, 2022

(65) Prior Publication Data

US 2023/0416716 A1 Dec. 28, 2023

(30) Foreign Application Priority Data

Oct. 27, 2020 (WO) ................. PCT/EP2020/080170

(51) Int. Cl.
*C12N 9/48* (2006.01)

(52) U.S. Cl.
CPC ...... *C12N 9/485* (2013.01); *C12Y 304/11001* (2013.01); *C12Y 304/14005* (2013.01)

(58) Field of Classification Search
CPC ...................................................... C12N 9/485
See application file for complete search history.

(56) References Cited

U.S. PATENT DOCUMENTS

2005/0158298 A1 7/2005 Monod et al.

FOREIGN PATENT DOCUMENTS

WO 2005/019251 A2 3/2005
WO 2006/034435 A2 3/2006
WO 2014/138983 A1 9/2014

OTHER PUBLICATIONS

Monod. Aminopeptidases and dipeptidyl-peptidases secreted by the dermatophyte Trichophyton rubrum. Microbiology (Reading). Jan. 2005;151(Pt 1):145-155.*

Fransceus. J Ind Microbiol Biotechnol. May 2017;44(4-5):687-695.*

Sanavia. Computational and Structural Biotechnology Journal, vol. 18, 2020, pp. 1968-1979.*

Studer. Residue mutations and their impact on protein structure and function: detecting beneficial and pathogenic changes. Biochem. J. (2013) 449, 581-594.*

Q5J6J3 (UniProtKB/Swiss-Prot Database. Dec. 11, 2019.*

Speck. Exploring the molecular linkage of protein stability traits for enzyme optimization by iterative truncation and evolution. Biochemistry. Jun. 19, 2012;51(24):4850-67.*

Nikitin I.G., et al., "Caroli Disease (Clinical Observation)," Russian Journal of Gastroenterology, Hepatology, Coloproctology, vol. 28(6):77-83 (2018).

Abbot, C. et al., "Binding to human dipeptidyl peptidase IV by adenosine deaminase and antibodies that inhibit ligand binding involves overlapping, discontinuous sites on a predicted beta propeller domain," Eur. J. Biochem, vol. 266(3):798-810 (1999).

Abdel-Ghany, M. et al., "Truncated Dipeptidyl Peptidase IV Is a Potent Anti-Adhesion and Anti-Metastasis Peptide for Rat Breast Cancer Cells," Invasion Metastasis, vol. 18:35-43 (1998).

Guenet, C. et al., "Isolation of the Leucine Aminopeptidase Gene from Aeromonas proteolytica," The Journal of Biological Chemistry, vol. 267(12):8390-8395 (1992).

International Preliminary Report on Patentability, PCT/EP2021/079522, dated May 2, 2023, 13 pages.

International Search Report and Written Opinion, PCT/EP2021/079522, dated Feb. 23, 2022, 19 pages.

Colombo I. et al., "Phase I dose-escalation study of the dual P13K/mTORC1/2 inhibitor Gedatolisib (PF-05212384) in combination with paclitaxel (P) and carboplatin (C) in patients (pts) with advanced solid tumours," Annals of Oncology—Abstract Book of the ESMO Virtual Congress, vol. 31(Supplement 4) (2020).

Forero A. et al., "Phase Ib study to assess the safety, tolerability, and clinical activity of gedatolisib in combination with palbociclib and either letrozole or fulvestrant in women with metastatic or locally advanced/recurrent breast cancer, (B2151009)," Cancer Research, American Association for Cancer Research Inc. NLD, vol. 78(4) (Supplement 1) Abstract Only (2018).

Forero-Torres A. et al., "Phase Ib study of gedatolisib in combination with palbociclib and endocrine therapy (ET) In women with estrogen receptor (ER) positive (+) metastatic breast cancer (MBC) (B2151009)," Journal of Clinical Oncology, vol. 36 (15)(Supplement 1):3 pages Abstract only (2018).

International Search Report and Written Opinion, PCT/US2022/038188, dated Oct. 28, 2022, 8 pages.

Vargaftig J. et al., "Phase 2 Trial of Single Agent Gedatolisib (PF-05212384), a Dual P13K/mTOR Inhibitor, for Adverse Prognosis and Relapse/Refractory AML: Clinical and Transcriptomic Results," BLOOD, vol. 132(1):5233 (2018).

Rubio-Tapia A., et. al., "Clinical staging and survival in refractory celiac disease: a single center experience," Gastroenterology, vol. 136(1): 19 pages (2009).

* cited by examiner

*Primary Examiner* — Yong D Pak
(74) *Attorney, Agent, or Firm* — Nelson Mullins Riley & Scarborough LLP; Jane E. Remillard, Esq.; Jeanne M. DiGiorgio

(57) ABSTRACT

The present disclosure relates to polypeptides with peptidase activity that are truncated variants of dipeptidylpeptidase IV (DPPIV) and leucine aminopeptidase (LAP) polypeptides, nucleic acids such as vectors encoding them, as well as host cells comprising the nucleic acids described herein and optionally expressing the polypeptides described herein. The polypeptides and nucleic acids described herein are useful in medical applications such as in the treatment of gluten-related disorders including celiac disease (CeD) and non-celiac gluten sensitivity (NCGS) as well as other diseases that may profit from a gluten-free diet (GFD).

9 Claims, 15 Drawing Sheets

Specification includes a Sequence Listing.

A)

B)

| Lane | Strain | Enzymatic activity [U/L] |
|---|---|---|
| 1 | Mark 12 Ladder | |
| 2 | 1 µg recombinant ruLAPII (Biomeva LAP-2 100.6 mg/mL) | |
| 3 | LP1 (pFJP6015.1) | 5 |
| 4 | LP1 (pFJP6015.7) | 110 |
| 5 | LP1 (pFJP6015.2) | 115 |
| **6** | **LP1 (pFJP6015.8)** | **2032** |
| 7 | LP1 (pFJP6015.3) | 740 |
| 8 | LP1 (pFJP6015.9) | 691 |
| 9 | LP1 (pFJP6015.4) | 856 |
| 10 | LP1 (pFJP6015.10) | 591 |
| 11 | LP1 (pFJP6015.5) | 1151 |
| 12 | LP1 (pFJP6015.11) | 1113 |
| **13** | **LP1 (pFJP6015.6)** | **1898** |

| Lane | Strain | Enzymatic activity [U/L] |
|---|---|---|
| **14** | **LP1 (pFJP6015.12)** | **1394** |
| 15 | LP1 (pFJP6015.13) | 47 |
| 16 | LP1 (pFJP6015.19) | 227 |
| 17 | LP1 (pFJP6015.14) | 1 |
| 18 | LP1 (pFJP6015.20) | 292 |
| **19** | **LP1 (pFJP6015.15)** | **1353** |
| 20 | LP1 (pFJP6015.21) | 59 |
| 21 | LP1 (pFJP6015.16) | 121 |
| 22 | LP1 (pFJP6015.22) | 1307 |
| 23 | LP1 (pFJP6015.17) | 1190 |
| 24 | LP1 (pFJP6015.23) | 201 |
| **25** | **LP1 (pFJP6015.18)** | **1614** |
| 26 | LP1 (pCKP6003.1) | 4325 |

A)

B)

| Lane | Strain | Enzymatic activity [U/L] |
|---|---|---|
| 1 | Mark 12 Ladder | |
| 2 | 1 µg recombinant ruLAPII (Biomeva LAP-2 100.6 mg/mL) | |
| 3 | LP1 (pFJP6014.1) | 0.2 |
| 4 | LP1 (pFJP6014.7) | 6.4 |
| 5 | LP1 (pFJP6014.2) | 5.9 |
| 6 | LP1 (pFJP6014.8) | 6.1 |
| 7 | LP1 (pFJP6014.3) | 0.0 |
| 8 | LP1 (pFJP6014.9) | 5.7 |
| 9 | LP1 (pFJP6014.4) | 0.0 |
| 10 | LP1 (pFJP6014.10) | 5.8 |
| 11 | LP1 (pFJP6014.5) | 0 |
| 12 | LP1 (pFJP6014.11) | 0 |
| **13** | **LP1 (pFJP6014.6)** | **11.6** |

| Lane | Strain | Enzymatic activity [U/L] |
|---|---|---|
| **14** | **LP1 (pFJP6014.12)** | **14.1** |
| **15** | **LP1 (pFJP6014.13)** | **26.1** |
| 16 | LP1 (pFJP6014.19) | 2 |
| 17 | LP1 (pFJP6014.14) | 7.0 |
| **18** | **LP1 (pFJP6014.20)** | **19.3** |
| **19** | **LP1 (pFJP6014.15)** | **7.1** |
| 20 | LP1 (pFJP6014.21) | 6.8 |
| 21 | LP1 (pFJP6014.16) | 0.1 |
| 22 | LP1 (pFJP6014.22) | 5.8 |
| 23 | LP1 (pFJP6014.17) | 0 |
| 24 | LP1 (pFJP6014.23) | 0.5 |
| 25 | LP1 (pFJP6014.18) | 0 |
| 26 | LP1 (pCKP6011.4) | 173.8 |

A)

B)

A)

B)

A)

B)

| Lane | Description | Titer [mg/L] | AMC Activity [U/L] | Specific Activity [U/mg] |
|---|---|---|---|---|
| 1 | Mark 12 | | | |
| 2 | LP1 pFJP6015.6 Load | 1742 | 5594 | 3.2 |
| 3 | LP1 pFJP6015.6 FT | 62 | 9 | 0.1 |
| 4 | LP1 pFJP6015.6 Elution | 94 | 1190 | 12.7 |
| 5 | LP1 pCKP6003.1 Load | 2220 | 9386 | 4.2 |
| 6 | LP1 pCKP6003.1 FT | 70 | 24 | 0.3 |
| 7 | LP1 pCKP6003.1 Elution | 290 | 3588 | 12.4 |

A)

B)

| Lane | Description | Titer [mg/L] | AMC Activity [U/L] | Specific Activity [U/mg] |
|---|---|---|---|---|
| 1 | Mark 12 | | | |
| 2 | LP1 pFJP6014.13 Load | 1082 | 287.0 | 0.3 |
| 3 | LP1 pFJP6014.13 FT | 39 | 7.5 | 0.2 |
| 4 | LP1 pFJP6014.13 Elution | 16 | 18.2 | 1.1 |
| 5 | LP1 pFJP6011.4 Load | 1702 | 1065.0 | 0.6 |
| 6 | LP1 pFJP6011.4 FT | 50 | 21.0 | 0.4 |
| 7 | LP1 pFJP6011.4 Elution | 147 | 218.6 | 1.5 |

DIPEPTIDYLPEPTIDASE AND LEUCINE AMINOPEPTIDASE POLYPEPTIDE VARIANTS

CROSS-REFERENCE TO RELATED APPLICATIONS

This application is a 35 U.S.C. 371 national stage filing of International Application No. PCT/EP2021/079522, filed on Oct. 25, 2021, which claims priority to International Application No. PCT/EP2020/080170, filed on Oct. 27, 2020, the contents of which are hereby incorporated by reference.

REFERENCE TO SEQUENCE LISTING

This application includes an electronically submitted sequence listing in .txt format. The .txt file contains a sequence listing entitled "ZSJ-001US_ST25.txt" created on Jan. 28, 2026 and is 26,934 bytes in size. The sequence listing contained in this .txt file is part of the specification and is hereby incorporated by reference herein in its entirety.

The present disclosure relates to polypeptides with peptidase activity that are truncated variants of dipeptidylpeptidase IV (DPPIV) and leucine aminopeptidase (LAP) polypeptides, nucleic acids such as vectors encoding them, as well as host cells comprising the nucleic acids described herein and optionally expressing the polypeptides described herein. The polypeptides and nucleic acids described herein are useful in medical applications such as in the treatment of gluten-related disorders including celiac disease (CeD) and non-celiac gluten sensitivity (NCGS) as well as other diseases that may profit from a gluten-free diet (GFD).

Wheat, barley, and rye are important staple foods in human diet throughout history, however the interaction between its component gluten, which is a mixture of digestion-resistant immunogenic peptides and the human body triggers an increasing variety of clinical, serological and morphological symptoms and the manifestation of autoimmune reactions. Gluten consists of polymeric glutenins and monomeric alcohol-soluble gliadins, which possess a high immunogenic or toxic potential. Due to the high content of proline and glutamine and low content of lysine and methionine, gliadin remains mainly stable to degradation by intraluminal proteases and intestinal brush-border membrane enzymes.

Gliadins and glutenins represent 80%-85% of gluten proteins. Gliadins are divided into α/β-, γ-, and ω-gliadin, and are monomeric proteins connected through intrachain disulfide bonds (α/β- γ-gliadins) or are not connected (w-gliadins). The N-terminal domain of α-gliadins contains a proline- and glutamine-rich heptapeptide PQPQPFP and pentapeptide PQQPY and the most characteristic immunogenic fragment.

Gluten-related disorders refer to three major types of human disorders: autoimmune celiac disease, wheat allergy and non-celiac gluten sensitivity.

Celiac disease (CeD) is a chronic autoimmune disorder in which patients develop a variety of intestinal and extra-intestinal symptoms, including specific neurological symptoms that are triggered by gluten immunogenic peptides (GIP), which are generated by the incomplete proteolysis during gluten digestion. These complex GIP are rich in proline and glutamine and are poorly digested by endogenous gastric, pancreatic and intestinal brush border proteases. GIP act as T-cell epitopes in genetically predisposed individuals (human leukocyte antigen HLA-DQ2 and/or DQ8) and trigger a CD4+ T-cell mediated immune response.

This results in the generation of cytotoxic T-cells and a local and systemic inflammatory reaction, which explain the disintegration of the epithelial lining of the small intestine and the extra-intestinal clinical symptoms and complications.

Patients may present themselves with diarrhea, vomiting, bloating, constipation, abdominal pain, weight loss, chronic fatigue and a variety of other symptoms. Secondary complications include but are not limited to an increased risk for cancer, osteoporosis and osteopenia, miscarriages and infertility in women and failure to thrive syndrome in children. About 40% of the population carries the genotypes HLA-DQ2 and/or HLA-DQ8 haplotypes that are required for the development of CeD. The overall prevalence ranges from 4.5% to 0.75%. The diagnosis of CeD is typically based on a combination of findings from a patient's clinical history and symptomatology, serologic testing and biopsies in the upper small intestine. In patients with typical symptoms, measurement of serum IgA antibodies to tissue transglutaminase (anti-tTG) is an excellent screening procedure with high sensitivity and specificity and is considered as the first line screening test. The blood of suspected individuals may also be tested for the presence of anti-endomysium (EMA)-IgA, anti-gliadin (AGA) or deamidated gliadin specific antibodies (DGP).

A further gluten-related complication is non-celiac gluten sensitivity (NCGS). NCGS is a syndrome characterized by intestinal and extra-intestinal symptoms related to the ingestion of gluten-containing food, in subjects that are not affected by CeD or wheat allergy (WA). The prevalence of NCGS is not clearly defined yet, however the prevalence has been estimated to be as high as 6% of the general population, depending on the population studied. In NCGS clinically symptoms reach from intestinal disturbances (abdominal pain, diarrhea, nausea, body mass loss, bloating, and flatulence) to cutaneous (erythema, eczema), general systemic manifestations (e.g. "foggy mind", headache, fatigue, bone and joint pain), anemia, behavioral (disturbance in attention, depression, and hyperactivity), and chronic ulcerative stomatitis. In contrast to CeD no specific genetic predisposition factor for NCGS has been identified so far and serological biomarkers are not available for NCGS, since the determination of celiac-related antibodies is not sensitive or specific to NCGS.

In contrast to CeD where the adaptive immune system is activated it seams that in NCGS responses from the innate immune system are upregulated. The NCGS patients' gastrointestinal tracts and their intestinal permeability is normal and the lesions in the histological picture of their duodenal mucosa are minor, but increased infiltration of eosinophils and basophils to the duodenal lamina propria and activation of circulating basophils have been observed in NCGS patients. Studies explored the relationship between the ingestion of gluten-containing food and the appearance of neurological and psychiatric disorders/symptoms like ataxia, peripheral neuropathy, schizophrenia, autism, depression, anxiety, and hallucinations (so-called gluten psychosis) and it has been suggested that gluten-related peptides can enter the systemic circulation and cause extraintestinal manifestations. Treatment strategies are under development, either targeting different steps of the disease pathogenesis or aiming at rendering the immunogenic peptides harmless before they reach the small intestinal mucosa. Currently, the only treatment option for CeD and NCGS is a strict GFD. The goal of this treatment is strictest avoidance of gluten intake and the generation of GIP, the external immune triggers of gluten-related disorders. The clinical treatment goal is resolution and/or avoidance of symptoms and prevention of the GIP-induced autoimmune reaction as well as improvement or avoidance of morphological and functional changes in the upper gastrointestinal (GI) tract, e.g. villous atrophy. Even very small traces of gluten that may be present in gluten-free products can trigger the immune reaction and clinical symptoms due to the lack of adherence to a totally GFD. Despite best efforts to adhere to a GFD, a significant subgroup of patients remains symptomatic, due to dietary mistakes and cross contamination, leading to inadvertent gluten ingestion.

In cases where CeD patients totally and strictly avoid gluten for a period of 3-4 months they become clinically, serologically and morphologically asymptomatic. This indicates that a permanent total enzymatic degradation of GIP qualifies as a treatment for CeD.

A combination of dipeptidylpeptidase IV of *Trichophyton rubrum* (ruDPPIV) and leucine aminopeptidase II of *Trichophyton rubrum* (ruLAPII) leads to the complete degradation of GIP.

The production of a short variant of ruLAPII (ruLAPII short) and ruDPPIV (ruDPPIV short) in a *P. pastoris* expression platform is described herein. These variants of ruLAPII and ruDPPIV were purified and tested for enzymatic activity (U/mg purified protein) together with their full-length variant. The purified shortened variants were analyzed by intact molecule mass spectroscopy.

It was found that the short variant of ruDPPIV showed similar enzymatic activity as the full-length variant. For ruLAPII, slightly lower activity was measured compared to the full-length variant:

ruDPPIV_short: 12.7 U/mg
ruDPPIV full-length: 12.4 U/mg
ruLAPII_short: 1.1 U/mg.
full-length: 1.5 U/mg Testing by mass spectroscopy to assess possible degradation revealed the following: For ruDPPIV short, full-length product but also degradation could be found in contrast to the full-length molecule ruDPPIV, where only degradation product could be identified. For ruLAPII short, no degradation was observed in contrast to the full-length molecule ruLAPII, where only degradation products were identified.

Based on the presented results, the short variants of ruDPPIV and ruLAPII show an improvement as full-length molecules could be identified in the mass spectroscopy (with full-length molecules, only degradation was identified) and the shortened variants still showed a similar enzymatic activity.

Accordingly, the invention is at least partially based on the surprising result that truncated ruDPPIV and ruLAPII polypeptides can be produced which retain activity and, at least partially, are resistant towards degradation.

SUMMARY

The present invention provides polypeptides with peptidase activity that are truncated variants of dipeptidylpeptidase IV (DPPIV), in particular ruDPPIV, or leucine aminopeptidase (LAP), in particular ruLAPII. ruDPPIV and ruLAPII are peptidases derived from the dermatophyte *Trichophyton rubrum.*

In one aspect, the present invention provides a polypeptide comprising a truncated dipeptidylpeptidase IV (DPPIV) polypeptide. In one embodiment, the truncation is an N-terminal and/or C-terminal truncation. In one embodiment, the truncated DPPIV polypeptide is a fragment of a wildtype DPPIV polypeptide.

In various embodiments, at least 1, at least 2, at least 3, at least 4, at least 5, at least 6, at least 7, at least 8, at least 9, at least 10, at least 11, at least 12, at least 13, or at least 14 amino acids are missing at the C-terminus compared to the wildtype DPPIV polypeptide. In various embodiments, 1, 2, 3, 4, 5, 6, 7, 8, 9, 10, 11, 12, 13, 14, or 15 amino acids are missing at the C-terminus compared to the wildtype DPPIV polypeptide. In these and other embodiments, at least 1 amino acid is missing at the N-terminus compared to the wildtype DPPIV polypeptide. In these and other embodiments, 1, or 2 amino acids are missing at the N-terminus compared to the wildtype DPPIV polypeptide. In one embodiment, at least 1 amino acid is missing at the N-terminus compared to the wildtype DPPIV polypeptide and at least 14 amino acids are missing at the C-terminus compared to the wildtype DPPIV polypeptide. In one embodiment, 1 amino acid is missing at the N-terminus compared to the wildtype DPPIV polypeptide and 14 amino acids are missing at the C-terminus compared to the wildtype DPPIV polypeptide.

In one embodiment, in the truncated DPPIV polypeptide (i) one or two amino acids are missing at the N-terminus and/or (ii) up to 15 amino acids are missing at the C-terminus compared to the wildtype DPPIV polypeptide. In one embodiment, 12 to 14 amino acids are missing at the C-terminus compared to the wildtype DPPIV polypeptide. In one embodiment, 13 or 14 amino acids are missing at the C-terminus compared to the wildtype DPPIV polypeptide.

In one embodiment, the wildtype DPPIV polypeptide has the amino acid sequence represented by SEQ ID NO: 1 or a variant thereof.

In various embodiments, a polypeptide comprising a truncated DPPIV polypeptide described herein comprises a truncated DPPIV polypeptide consisting of an amino acid sequence represented by residues 1-745, 1-746, 1-747, 1-748, 1-749, 1-750, 1-751, 1-752, 1-753, 1-754, 1-755, 1-756, 1-757, 1-758, or 1-759 of SEQ ID NO: 1 or a variant thereof. In various embodiments, a polypeptide comprising a truncated DPPIV polypeptide described herein comprises a truncated DPPIV polypeptide consisting of an amino acid sequence represented by residues 2-745, 2-746, 2-747, 2-748, 2-749, 2-750, 2-751, 2-752, 2-753, 2-754, 2-755, 2-756, 2-757, 2-758, or 2-759 of SEQ ID NO: 1 or a variant thereof.

In a further aspect, the present invention provides a polypeptide selected from the group consisting of:

(i) a polypeptide comprising a truncated DPPIV polypeptide consisting of an amino acid sequence represented by residues 1-748 of SEQ ID NO: 1;
(ii) a polypeptide comprising a truncated DPPIV polypeptide consisting of an amino acid sequence represented by residues 1-747 of SEQ ID NO: 1;
(iii) a polypeptide comprising a truncated DPPIV polypeptide consisting of an amino acid sequence represented by residues 1-746 of SEQ ID NO: 1;
(iv) a polypeptide comprising a truncated DPPIV polypeptide consisting of an amino acid sequence represented by residues 1-745 of SEQ ID NO: 1;
(v) a polypeptide comprising a truncated DPPIV polypeptide consisting of an amino acid sequence represented by residues 2-748 of SEQ ID NO: 1;
(vi) a polypeptide comprising a truncated DPPIV polypeptide consisting of an amino acid sequence represented by residues 2-747 of SEQ ID NO: 1

(vii) a polypeptide comprising a truncated DPPIV polypeptide consisting of an amino acid sequence represented by residues 2-746 of SEQ ID NO: 1; and (viii) a polypeptide comprising a truncated DPPIV polypeptide consisting of an amino acid sequence represented by residues 2-745 of SEQ ID NO: 1.

In one embodiment, the polypeptide comprising a truncated DPPIV polypeptide described herein is derived from *Trichophyton rubrum.*

In one embodiment, the polypeptide comprising a truncated DPPIV polypeptide described herein cleaves the dipeptide motive NH2-X-Pro off the N-terminal end of polypeptides.

In one embodiment, the polypeptide comprising a truncated DPPIV polypeptide described herein is produced in *Pichia pastoris.*

In different embodiments, a polypeptide comprising a truncated DPPIV polypeptide described herein does not comprise the sequence of the wildtype DPPIV polypeptide from which it is derived, for example the amino acid sequence represented by SEQ ID NO: 1 or a variant thereof, and preferably does not comprise the non-truncated sequence of the wildtype DPPIV polypeptide from which it is derived, for example the amino acid sequence represented by SEQ ID NO: 1 or a variant thereof, in particular the sequence of the wildtype DPPIV polypeptide from which it is derived, for example the amino acid sequence represented by SEQ ID NO: 1 or a variant thereof, truncated to a lesser extent compared to the truncated DPPIV polypeptide. For example, in the case of a polypeptide comprising a truncated DPPIV polypeptide wherein 14 amino acids are missing at the C-terminus compared to the wildtype DPPIV polypeptide, the polypeptide does not comprise the amino acid sequence of the non-truncated, i.e., the wildtype, DPPIV polypeptide and preferably does not comprise the amino acid sequence of the wildtype DPPIV polypeptide wherein, for example, 13 or less amino acids are missing at the C-terminus compared to the wildtype DPPIV polypeptide. Similarly, for example, in the case of a polypeptide comprising a truncated DPPIV polypeptide which comprises a truncated DPPIV polypeptide consisting of an amino acid sequence represented by residues 1-746 of the wildtype DPPIV polypeptide, the polypeptide does not comprise the amino acid sequence of the non-truncated, i.e., the wildtype, DPPIV polypeptide and preferably does not comprise the amino acid sequence represented by residues 1-747 or more residues of the wildtype DPPIV polypeptide. In other words, those sequences that may be present at the N- and/or C-terminus of a truncated DPPIV polypeptide in a polypeptide comprising a truncated DPPIV polypeptide described herein do preferably not correspond to the amino acids that are truncated or missing in the truncated DPPIV polypeptide compared to the wildtype DPPIV polypeptide. Thus, a polypeptide comprising a truncated DPPIV polypeptide described herein does not comprise the full-length sequence of the wildtype DPPIV polypeptide from which it is derived or a continuous amino acid sequence of the full-length sequence of the wildtype DPPIV polypeptide longer than the amino acid sequence of the truncated DPPIV polypeptide.

In one embodiment, if a certain number of amino acids is missing at the C-terminus compared to the wildtype DPPIV polypeptide a polypeptide comprising a truncated DPPIV polypeptide described herein does not comprise an amino acid sequence represented by the amino acids missing at the C-terminus compared to the wildtype DPPIV polypeptide. In various embodiments, a polypeptide comprising a truncated DPPIV polypeptide described herein does not comprise an amino acid sequence represented by residues 747-760, 748-760, 749-760, 750-760, 751-760, 752-760, 753-760, 754-760, or 755-760 of SEQ ID NO: 1 or a variant thereof.

The polypeptide comprising a truncated DPPIV polypeptide described herein retains activity of the wildtype DPPIV polypeptide from which it is derived. The polypeptide comprising a truncated DPPIV polypeptide described herein retains at least 50%, at least 60%, at least 70%, at least 80%, or at least 90% of the activity of the wildtype DPPIV polypeptide from which it is derived.

In a further aspect, the present invention provides a polypeptide consisting of a truncated DPPIV polypeptide described herein, which is optionally fused to a signal peptide, for example a signal peptide useful for secreted expression in *Pichia pastoris*, wherein the signal peptide is preferably fused to the N-terminus of the truncated DPPIV polypeptide.

In one embodiment, polypeptide comprising a truncated DPPIV polypeptide and/or a truncated DPPIV polypeptide consists of the amino acid sequence shown in SEQ ID NO: 3.

In a further aspect, the present invention provides a polypeptide comprising a truncated leucine aminopeptidase (LAP) polypeptide. In one embodiment, the truncation is an N-terminal and/or C-terminal truncation. In one embodiment, the truncated LAP polypeptide is a fragment of a wildtype LAP polypeptide.

In various embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 amino acids are missing at the C-terminus compared to the wildtype LAP polypeptide. In various embodiments, 1, 2, 3, 4, 5, 6, 7, 8, 9, 10, 11, 12, 13, 14, 15, 16, 17, 18, 19, 20, 21, 22, or 23 amino acids are missing at the C-terminus compared to the wildtype LAP polypeptide. In these and other embodiments, at least 1, at least 2, at least 3, at least 4, at least 5, or at least 6 amino acids are missing at the N-terminus compared to the wildtype LAP polypeptide. In these and other embodiments, 1, 2, 3, 4, 5, 6, or 7 amino acids are missing at the N-terminus compared to the wildtype LAP polypeptide. In one embodiment, at least 6 amino acid are missing at the N-terminus compared to the wildtype LAP polypeptide and at least 22 amino acids are missing at the C-terminus compared to the wildtype LAP polypeptide. In one embodiment, 6 amino acids are missing at the N-terminus compared to the wildtype LAP polypeptide and 22 amino acids are missing at the C-terminus compared to the wildtype LAP polypeptide In one embodiment, in the truncated LAP polypeptide (i) up to 7 amino acids are missing at the N-terminus, and/or (ii) up to 23 amino acids are missing at the C-terminus compared to wildtype LAP polypeptide. In one embodiment, 4 to 6 amino acids are missing at the N-terminus compared to wildtype LAP polypeptide. In one embodiment, 6 amino acids are missing at the N-terminus compared to wildtype LAP polypeptide. In one embodiment, between 20 to 22 amino acids are missing at the C-terminus compared to wildtype LAP polypeptide. In one embodiment, 8, 16, 21, or 22 amino acids are missing at the C-terminus compared to wildtype LAP polypeptide. In one embodiment, 22 amino acids are missing at the C-terminus compared to wildtype LAP polypeptide.

In one embodiment, the wildtype LAP polypeptide has the amino acid sequence represented by SEQ ID NO: 2 or a variant thereof.

In various embodiments, a polypeptide comprising a truncated LAP polypeptide described herein comprises a truncated LAP polypeptide consisting of an amino acid sequence represented by residues 1-456, 1-457, 1-458, 1-459, 1-460, 1-461, 1-462, 1-463, 1-464, 1-465, 1-466, 1-467, 1-468, 1-469, 1-470, 1-471, 1-472, 1-473, 1-474, 1-475, 1-476, 1-477, or 1-478 of SEQ ID NO: 2 or a variant thereof. In various embodiments, a polypeptide comprising a truncated LAP polypeptide described herein comprises a truncated LAP polypeptide consisting of an amino acid sequence represented by residues 2-456, 2-457, 2-458, 2-459, 2-460, 2-461, 2-462, 2-463, 2-464, 2-465, 2-466, 2-467, 2-468, 2-469, 2-470, 2-471, 2-472, 2-473, 2-474, 2-475, 2-476, 2-477, or 2-478 of SEQ ID NO: 2 or a variant thereof. In various embodiments, a polypeptide comprising a truncated LAP polypeptide described herein comprises a truncated LAP polypeptide consisting of an amino acid sequence represented by residues 3-456, 3-457, 3-458, 3-459, 3-460, 3-461, 3-462, 3-463, 3-464, 3-465, 3-466, 3-467, 3-468, 3-469, 3-470, 3-471, 3-472, 3-473, 3-474, 3-475, 3-476, 3-477, or 3-478 of SEQ ID NO: 2 or a variant thereof. In various embodiments, a polypeptide comprising a truncated LAP polypeptide described herein comprises a truncated LAP polypeptide consisting of an amino acid sequence represented by residues 4-456, 4-457, 4-458, 4-459, 4-460, 4-461, 4-462, 4-463, 4-464, 4-465, 4-466, 4-467, 4-468, 4-469, 4-470, 4-471, 4-472, 4-473, 4-474, 4-475, 4-476, 4-477, or 4-478 of SEQ ID NO: 2 or a variant thereof. In various embodiments, a polypeptide comprising a truncated LAP polypeptide described herein comprises a truncated LAP polypeptide consisting of an amino acid sequence represented by residues 5-456, 5-457, 5-458, 5-459, 5-460, 5-461, 5-462, 5-463, 5-464, 5-465, 5-466, 5-467, 5-468, 5-469, 5-470, 5-471, 5-472, 5-473, 5-474, 5-475, 5-476, 5-477, or 5-478 of SEQ ID NO: 2 or a variant thereof. In various embodiments, a polypeptide comprising a truncated LAP polypeptide described herein comprises a truncated LAP polypeptide consisting of an amino acid sequence represented by residues 6-456, 6-457, 6-458, 6-459, 6-460, 6-461, 6-462, 6-463, 6-464, 6-465, 6-466, 6-467, 6-468, 6-469, 6-470, 6-471, 6-472, 6-473, 6-474, 6-475, 6-476, 6-477, or 6-478 of SEQ ID NO: 2 or a variant thereof. In various embodiments, a polypeptide comprising a truncated LAP polypeptide described herein comprises a truncated LAP polypeptide consisting of an amino acid sequence represented by residues 7-456, 7-457, 7-458, 7-459, 7-460, 7-461, 7-462, 7-463, 7-464, 7-465, 7-466, 7-467, 7-468, 7-469, 7-470, 7-471, 7-472, 7-473, 7-474, 7-475, 7-476, 7-477, or 7-478 of SEQ ID NO: 2 or a variant thereof. In various embodiments, a polypeptide comprising a truncated LAP polypeptide described herein comprises a truncated LAP polypeptide consisting of an amino acid sequence represented by residues 8-456, 8-457, 8-458, 8-459, 8-460, 8-461, 8-462, 8-463, 8-464, 8-465, 8-466, 8-467, 8-468, 8-469, 8-470, 8-471, 8-472, 8-473, 8-474, 8-475, 8-476, 8-477, or 8-478 of SEQ ID NO: 2 or a variant thereof.

In a further aspect, the present invention provides a polypeptide selected from the group consisting of:

(i) a polypeptide comprising a truncated LAP polypeptide consisting of an amino acid sequence represented by residues 7-471 of SEQ ID NO: 2;

(ii) a polypeptide comprising a truncated LAP polypeptide consisting of an amino acid sequence represented by residues 7-463 of SEQ ID NO: 2;

(iii) a polypeptide comprising a truncated LAP polypeptide consisting of an amino acid sequence represented by residues 7-458 of SEQ ID NO: 2;

(iv) a polypeptide comprising a truncated LAP polypeptide consisting of an amino acid sequence represented by residues 7-457 of SEQ ID NO: 2; and (v) a polypeptide comprising a truncated LAP polypeptide consisting of an amino acid sequence represented by residues 7-456 of SEQ ID NO: 2.

In one embodiment, the polypeptide comprising a truncated LAP polypeptide described herein is derived from *Trichophyton rubrum.*

In one embodiment, the polypeptide comprising a truncated LAP polypeptide described herein cleaves single amino acids off the N-terminal end of polypeptides, except when these are connected to proline in an NH2-X-Pro sequence.

In one embodiment, the polypeptide comprising a truncated LAP polypeptide described herein is produced in *Pichia pastoris.*

In different embodiments, a polypeptide comprising a truncated LAP polypeptide described herein does not comprise the sequence of the wildtype LAP polypeptide from which it is derived, for example the amino acid sequence represented by SEQ ID NO: 2 or a variant thereof, and preferably does not comprise the non-truncated sequence of the wildtype LAP polypeptide from which it is derived, for example the amino acid sequence represented by SEQ ID NO: 2 or a variant thereof, in particular the sequence of the wildtype LAP polypeptide from which it is derived, for example the amino acid sequence represented by SEQ ID NO: 2 or a variant thereof, truncated to a lesser extent compared to the truncated LAP polypeptide. For example, in the case of a polypeptide comprising a truncated LAP polypeptide wherein 22 amino acids are missing at the C-terminus compared to the wildtype LAP polypeptide, the polypeptide does not comprise the amino acid sequence of the non-truncated, i.e., the wildtype, LAP polypeptide and preferably does not comprise the amino acid sequence of the wildtype LAP polypeptide wherein, for example, 21 or less amino acids are missing at the C-terminus compared to the wildtype LAP polypeptide. Similarly, for example, in the case of a polypeptide comprising a truncated LAP polypeptide which comprises a truncated LAP polypeptide consisting of an amino acid sequence represented by residues 1-457 of the wildtype LAP polypeptide, the polypeptide does not comprise the amino acid sequence of the non-truncated, i.e., the wildtype, LAP polypeptide and preferably does not comprise the amino acid sequence represented by residues 1-458 or more residues of the wildtype LAP polypeptide. Similarly, for example, in the case of a polypeptide comprising a truncated LAP polypeptide which comprises a truncated LAP polypeptide consisting of an amino acid sequence represented by residues 7-457 of the wildtype LAP polypeptide, the polypeptide does not comprise the amino acid sequence of the non-truncated, i.e., the wildtype, LAP polypeptide and preferably does not comprise the amino acid sequence represented by residues 6-457, 7-458, or 6-458 or more residues of the wildtype LAP polypeptide. In other words, those sequences that may be present at the N- and/or C-terminus of a truncated LAP polypeptide in a polypeptide comprising a truncated LAP polypeptide described herein do preferably not correspond to the amino acids that are truncated or missing in the truncated LAP polypeptide compared to the wildtype LAP polypeptide. Thus, a polypeptide comprising a truncated LAP polypeptide described herein does not comprise the full-length sequence of the wildtype LAP polypeptide from which it is derived or a continuous amino acid sequence of the full-length sequence of the wildtype LAP polypeptide longer than the amino acid sequence of the truncated LAP polypeptide.

In one embodiment, if a certain number of amino acids is missing at the N-terminus and/or C-terminus compared to the wildtype LAP polypeptide a polypeptide comprising a truncated LAP polypeptide described herein does not comprise an amino acid sequence represented by the amino acids missing at the N-terminus and/or C-terminus compared to the wildtype LAP polypeptide. In various embodiments, a polypeptide comprising a truncated LAP polypeptide described herein does not comprise an amino acid sequence represented by residues 1-6 of SEQ ID NO: 2 or a variant thereof and/or does not comprise an amino acid sequence represented by residues 458-479, 459-479, 460-479, 461-479, 462-479, 463-479, 464-479, 465-479, 466-479, 467-479, 468-479, 469-479, 470-479, 471-479, 472-479, 473-479, or 474-479 of SEQ ID NO: 2 or a variant thereof.

The polypeptide comprising a truncated LAP polypeptide described herein retains activity of the wildtype LAP polypeptide from which it is derived. The polypeptide comprising a truncated LAP polypeptide described herein retains at least 50%, at least 60%, at least 70%, at least 80%, or at least 90% of the activity of the wildtype LAP polypeptide from which it is derived.

In a further aspect, the present invention provides a polypeptide consisting of a truncated LAP polypeptide described herein, which is optionally fused to a signal peptide, for example a signal peptide useful for secreted expression in *Pichia pastoris*, wherein the signal peptide is preferably fused to the N-terminus of the truncated LAP polypeptide.

In one embodiment, polypeptide comprising a truncated LAP polypeptide and/or a truncated LAP polypeptide consists of the amino acid sequence shown in SEQ ID NO: 4.

In a further aspect, the present invention provides a composition comprising:

(i) a polypeptide comprising a truncated DPPIV polypeptide described herein;
(ii) a polypeptide comprising a truncated LAP polypeptide described herein; or
(iii) a combination of (i) and (ii).

In a further aspect, the present invention provides a composition comprising:

(i) a polypeptide comprising a truncated DPPIV polypeptide described herein; and
(ii) a polypeptide comprising a truncated LAP polypeptide described herein.

In one embodiment, in a composition described herein, a truncated DPPIV polypeptide described herein comprises at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% of the DPPIV polypeptide in the composition. In one embodiment, in a composition described herein, a truncated LAP polypeptide described herein comprises at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% of the LAP polypeptide in the composition. For example, in a composition described herein, a truncated DPPIV polypeptide described herein comprises at least 70% of the DPPIV polypeptide in the composition and a truncated LAP polypeptide described herein comprises at least 70% of the LAP polypeptide in the composition. For example, in a composition described herein, a truncated DPPIV polypeptide described herein comprises at least 80% of the DPPIV polypeptide in the composition and a truncated LAP polypeptide described herein comprises at least 80% of the LAP polypeptide in the composition. For example, in a composition described herein, a truncated DPPIV polypeptide described herein comprises at least 90% of the DPPIV polypeptide in the composition and a truncated LAP polypeptide described herein comprises at least 90% of the LAP polypeptide in the composition. For example, in a composition described herein, a truncated DPPIV polypeptide described herein comprises at least 95% of the DPPIV polypeptide in the composition and a truncated LAP polypeptide described herein comprises at least 95% of the LAP polypeptide in the composition. For example, in a composition described herein, a truncated DPPIV polypeptide described herein comprises at least 98% of the DPPIV polypeptide in the composition and a truncated LAP polypeptide described herein comprises at least 98% of the LAP polypeptide in the composition.

In one embodiment, the weight ratio of a polypeptide comprising a truncated DPPIV polypeptide described herein and a polypeptide comprising a truncated LAP polypeptide described herein is between 1:20 and 1:5, preferably between 1:15 and 1:7.5, more preferably about 1:9.5.

In one embodiment, the composition described herein completely degrades e.g. the following alpha-gliadin 33-mer peptide:

```
LQLQPFPQPQLPYPQPQLPYPQPQLPYPQPQPF
```

In one embodiment, the composition described herein is a pharmaceutical composition.

In a further aspect, the present invention provides a composition described herein for pharmaceutical use.

In a further aspect, the present invention provides a composition described herein for use in the treatment of gluten-related disorders.

In one embodiment, the composition described herein is an oral composition, in particular a liquid oral composition.

In a further aspect, the present invention provides a nucleic acid encoding a polypeptide comprising a truncated DPPIV polypeptide described herein. In a further aspect, the present invention provides a cell which is transfected with said nucleic acid.

In a further aspect, the present invention provides a nucleic acid encoding a polypeptide comprising a truncated LAP polypeptide described herein. In a further aspect, the present invention provides a cell which is transfected with said nucleic acid.

In a further aspect, the present invention provides the polypeptides and compositions described herein for pharmaceutical use. In one embodiment, the pharmaceutical use comprises a therapeutic or prophylactic treatment of gluten-related disorder in a subject.

In a further aspect, the present invention provides a method of treating or preventing gluten-related disorders in a subject comprising administering to the subject a polypeptide or composition described herein.

In one aspect, the invention relates to a polypeptide or composition described herein for use in a method described herein.

DETAILED DESCRIPTION

Figure 1:
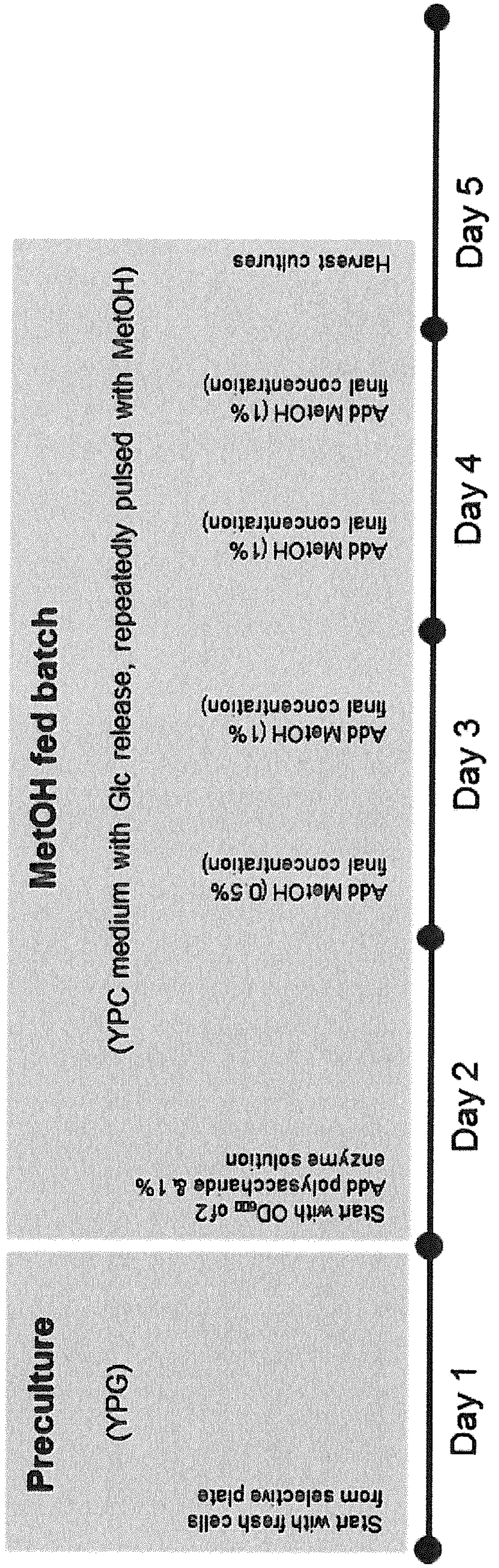
FIG. 1. Overview of *P. pastoris* AOX1 screening. Glucose release is done by enzymatic digestion of polysaccharide (EnPump200 system, EnPresso GmbH). The promoter is induced by limiting Methanol concentrations.

Although the present disclosure is described in detail below, it is to be understood that this disclosure is not limited to the particular methodologies, protocols and reagents described herein as these may vary. It is also to be understood that the terminology used herein is for the purpose of describing particular embodiments only and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means ±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term “comprising” is used in the context of the present document to indicate that further members may optionally be present in addition to the members of the list introduced by “comprising”. It is, however, contemplated as a specific embodiment of the present disclosure that the term “comprising” encompasses the possibility of no further members being present, i.e., for the purpose of this embodiment “comprising” is to be understood as having the meaning of “consisting of” or “consisting essentially of”. Several documents are cited throughout the text of this specification. Each of the documents cited herein (including all patents, patent applications, scientific publications, manufacturer’s specifications, instructions, etc.), whether supra or infra, are hereby incorporated by reference in their entirety. Nothing herein is to be construed as an admission that the present disclosure was not entitled to antedate such disclosure.

Definitions

In the following, definitions will be provided which apply to all aspects of the present disclosure. The following terms have the following meanings unless otherwise indicated. Any undefined terms have their art recognized meanings.

Terms such as “reduce”, “decrease”, “inhibit” or “impair” as used herein relate to an overall reduction or the ability to cause an overall reduction, preferably of at least 5%, at least 10%, at least 20%, at least 50%, at least 75% or even more, in the level. These terms include a complete or essentially complete inhibition, i.e., a reduction to zero or essentially to zero.

Terms such as “increase”, “enhance” or “exceed” preferably relate to an increase or enhancement by at least 10%, at least 20%, at least 30%, at least 40%, at least 50%, at least 80%, at least 100%, at least 200%, at least 500%, or even more.

As used herein, the terms “peptidase”, “protease”, “proteolytic enzyme” and “peptide hydrolase” are synonyms and may be used interchangeably. Peptidases include all enzymes that catalyse the cleavage of the peptide bonds (CO—NH) of proteins or peptides, digesting these proteins or peptides into peptides or free amino acids. Exopeptidases act near the ends of polypeptide chains at the amino (N)- or carboxy (C)-terminus. Those acting at a free N-terminus liberate a single amino acid residue and are termed aminopeptidases.

Dipeptidylpeptidase IV or dipeptidylpeptidase 4 (abbreviation: DPPIV or DPP4) is a serine exopeptidase that cleaves X-proline or X-alanine dipeptides from the N-terminus of polypeptides.

Leucine aminopeptidase (abbreviation: LAP) is an enzyme that preferentially catalyzes the hydrolysis of leucine residues at the N-terminus of peptides and proteins. Other N-terminal residues can also be cleaved, however.

Dipeptidylpeptidase IV of *Trichophyton rubrum* (ruDPPIV) and leucine aminopeptidase II of *Trichophyton rubrum* (ruLAPII) are preferred embodiments of DPPIV and LAP polypeptides, respectively. ruLAPII, a leucine aminopeptidase, cleaves single amino acids off the N-terminal end of polypeptides, except when these are connected to proline in an NH2-X-Pro sequence. ruDPPIV, a dipeptidyl peptidase, selectively cleaves the dipeptide motive NH2-X-Pro off the N-terminal end of polypeptides. Simultaneous application of both enzymes therefore can be used to degrade proline-rich, digestion-resistant, GIP.

Figure 14:
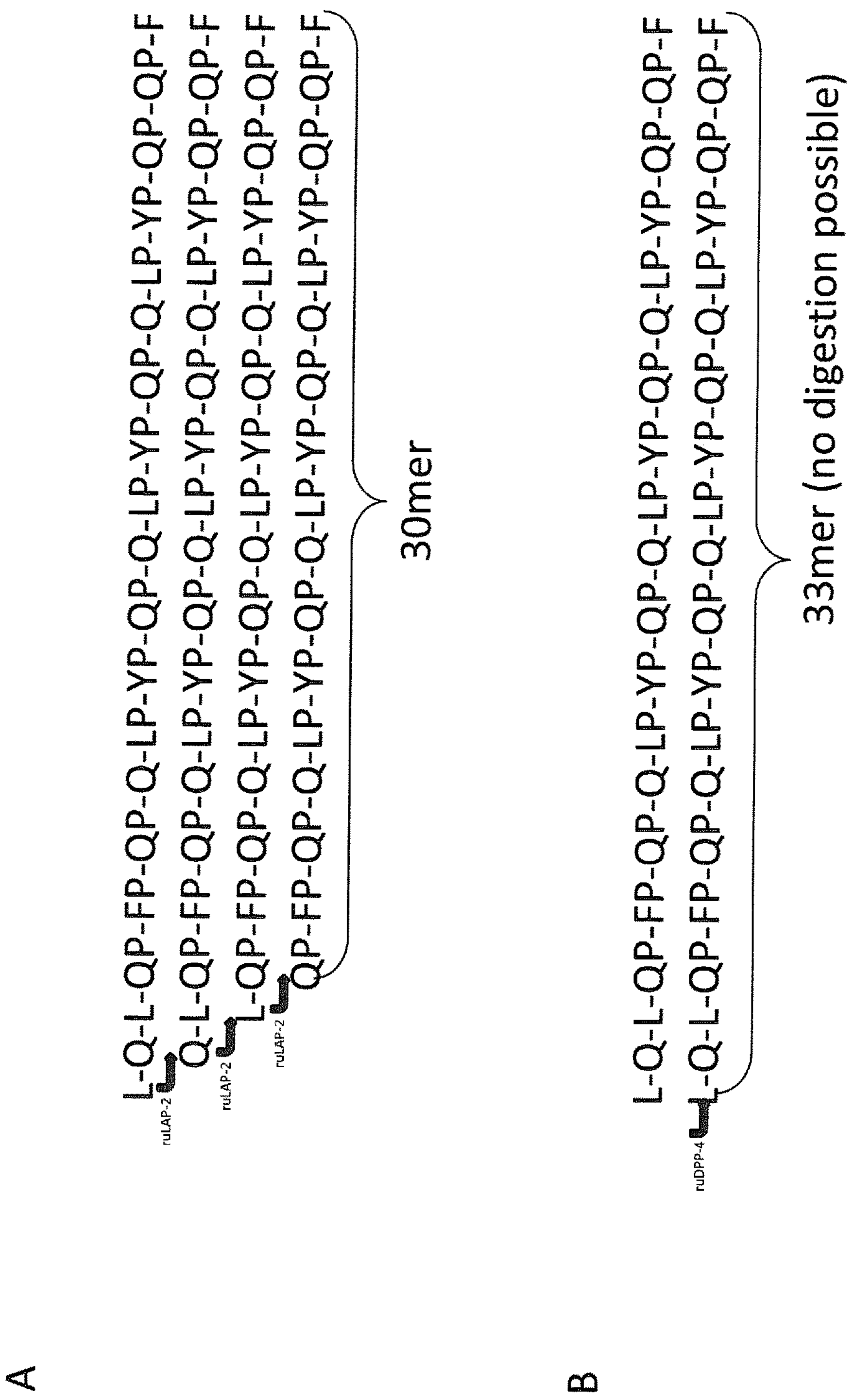
FIG. 14. Partial degradation of the 33-mer by ruLAPII (A) (SEQ ID NOs: 7-10)/No degradation of the 33-mer by ruDPPIV (B) (SEQ ID NO: 7).
Figure 15:
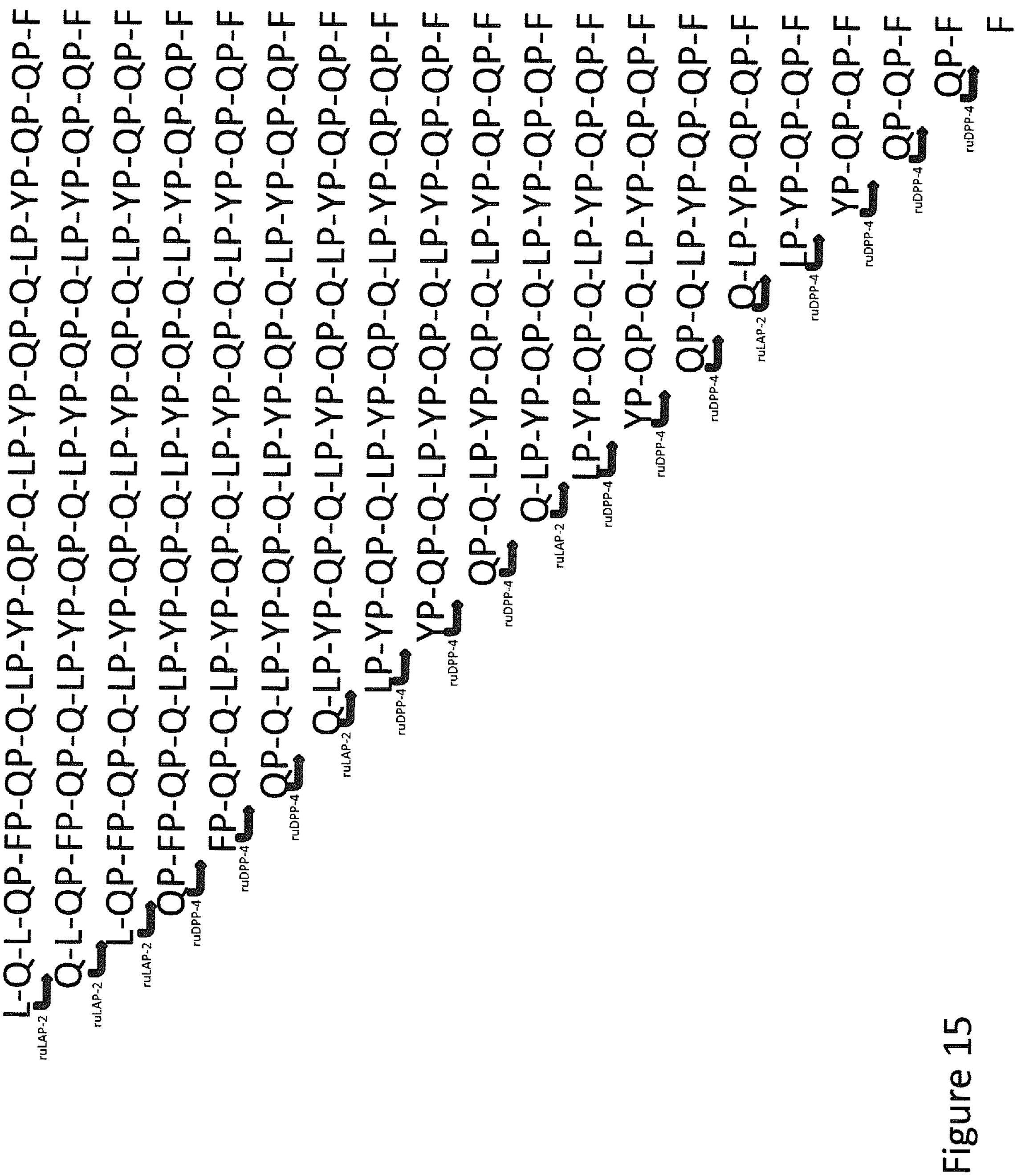
FIG. 15. Synergistic mode of action of ruLAPII and ruDPPIV (SEQ ID NOs: 7-25).

None of both, ruDPPIV and ruLAPII is capable on its own to completely degrade the x-gliadin 33-mer, a gluten-derived highly immunogenic peptide, which represents a well described immunoreactive GIP and functions as accepted model peptide. The x-gliadin 33-mer contains two of the most potent celiac disease-related T-cell epitopes in multiple copies and is described as being highly degradation resistant. While ruLAPII can remove the first 3 amino acids from the N-terminus, the degradation cannot proceed beyond that point due to the QP-motif that follows next (see FIG. 14A). ruDPPIV on the other hand does not affect the 33-mer since the enzyme specifically cleaves X-Pro dipeptide motifs but not the amino acids present in the N-terminus of the 33-mer (see FIG. 14B). When present in combination, however, ruDPPIV and ruLAPII can completely degrade the gliadin 33-mer (FIG. 15). For complete degradation ruDPPIV and ruLAPII must act synergistically.

A ruDPPIV polypeptide may have an amino acid sequence comprising the amino acid sequence of SEQ ID NO: 1, or an amino acid sequence having at least 99%, 98%, 97%, 96%, 95%, 90%, 85%, or 80% identity to the amino acid sequence of SEQ ID NO: 1.

A ruLAPII polypeptide may have an amino acid sequence comprising the amino acid sequence of SEQ ID NO: 2, or an amino acid sequence having at least 99%, 98%, 97%, 96%, 95%, 90%, 85%, or 80% identity to the amino acid sequence of SEQ ID NO: 2.

The polypeptides described herein comprise a truncated dipeptidylpeptidase IV (DPPIV) polypeptide such as truncated ruDPPIV or a truncated leucine aminopeptidase (LAP) polypeptide such as truncated ruLAPII. The truncated DPPIV polypeptide such as truncated ruDPPIV or truncated leucine aminopeptidase (LAP) polypeptide such as truncated ruLAPII may be part of a chimeric or fusion protein.

“Chimeric protein” or “fusion protein” comprises a truncated DPPIV polypeptide such as truncated ruDPPIV or truncated leucine aminopeptidase (LAP) polypeptide such as truncated ruLAPII linked at the N-terminus and/or C-terminus to one or more other amino acid sequences.

The term “one or more other amino acid sequences” in the case of a truncated DPPIV polypeptide such as truncated ruDPPIV refers to (an) amino acid sequence(s) corresponding to a protein that is not substantially homologous to the DPPIV polypeptide such as ruDPPIV. Within the fusion protein, the truncated DPPIV polypeptide such as truncated ruDPPIV and the one or more other amino acid sequences are fused with one another. The one or more other amino acid sequences can be fused to the N-terminus and/or C-terminus of the truncated DPPIV polypeptide such as truncated ruDPPIV. However, fusion of the one or more other amino acid sequences to the truncated DPPIV polypeptide such as truncated ruDPPIV does not result in addition of amino acid sequences to the truncated DPPIV polypeptide such as truncated ruDPPIV which are present in the complete, i.e. non-truncated, DPPIV polypeptide such as ruDPPIV.

The term “one or more other amino acid sequences” in the case of a truncated leucine aminopeptidase (LAP) polypeptide such as truncated ruLAPII refers to (an) amino acid sequence(s) corresponding to a protein that is not substantially homologous to the leucine aminopeptidase (LAP) polypeptide such as ruLAPII. Within the fusion protein, the truncated leucine aminopeptidase (LAP) polypeptide such as truncated ruLAPII and the one or more other amino acid sequences are fused with one another. The one or more other amino acid sequences can be fused to the N-terminus and/or C-terminus of the truncated leucine aminopeptidase (LAP) polypeptide such as truncated ruLAPII. However, fusion of the one or more other amino acid sequences to the truncated leucine aminopeptidase (LAP) polypeptide such as truncated ruLAPII does not result in addition of amino acid sequences to the truncated leucine aminopeptidase (LAP) polypeptide such as truncated ruLAPII which are present in the complete, i.e. non-truncated, leucine aminopeptidase (LAP) polypeptide such as ruLAPII. In one embodiment, the one or more other amino acid sequences comprise a signal sequence, e.g. a heterologous signal sequence, that is fused to truncated polypeptide, e.g., to the N-terminus of the truncated polypeptide.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" or "polypeptide" refers to large peptides, in particular peptides having more than about 150 amino acids, but the terms "peptide", "protein" and "polypeptide" are used herein usually as synonyms.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

By "variant" herein is meant an amino acid sequence that differs from a parent amino acid sequence by virtue of at least one amino acid modification. The parent amino acid sequence may be a naturally occurring or wild type (WT) amino acid sequence or may be a modified version of a wild type amino acid sequence. Preferably, the variant amino acid sequence has at least one amino acid modification compared to the parent amino acid sequence, e.g., from 1 to about 20 amino acid modifications, and preferably from 1 to about 10 or from 1 to about 5 amino acid modifications compared to the parent.

By "wild type" or "WT" or "native" herein is meant an amino acid sequence that is found in nature, including allelic variations. A wild type amino acid sequence, peptide or protein has an amino acid sequence that has not been intentionally modified.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all mutants, splice variants, posttranslationally modified variants, conformations, isoforms, allelic variants, species variants, and species homologs, in particular those which are naturally occurring. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

Preferably the degree of similarity, preferably identity between a given amino acid sequence and an amino acid sequence which is a variant of said given amino acid sequence will be at least about 60%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, in some embodiments continuous amino acids. In some embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS: needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences. "Sequence identity" between two nucleic acid sequences indicates the percentage of nucleotides that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi?PAGE_TYPE=BlastSearch&BLAST_SPEC=blast2seq&LINK_LOC=align2seq). In some embodiments, the algorithm parameters used for BLASTN algorithm on the NCBI website include: (i) Expect Threshold set to 10; (ii) Word Size set to 28; (iii) Max matches in a query range set to 0; (iv) Match/Mismatch Scores set to 1, −2; (v) Gap Costs set to Linear; and (vi) the filter for low complexity regions being used. In some embodiments, the algorithm parameters used for BLASTP algorithm on the NCBI website include: (i) Expect Threshold set to 10; (ii) Word Size set to 3; (iii) Max matches in a query range set to 0; (iv) Matrix set to BLOSUM62; (v) Gap Costs set to Existence: 11 Extension: 1; and (vi) conditional compositional score matrix adjustment.

Percentage identity is obtained by determining the number of identical positions at which the sequences to be compared correspond, dividing this number by the number of positions compared (e.g., the number of positions in the reference sequence) and multiplying this result by 100.

In some embodiments, the degree of similarity or identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments continuous nucleotides. In some embodiments, the degree of similarity or identity is given for the entire length of the reference sequence. Homologous amino acid sequences exhibit according to the disclosure at least 40%, in particular at least 50%, at least 60%, at least 70%, at least 80%, at least 90% and preferably at least 95%, at least 98%, or at least 99% identity of the amino acid residues.

According to the invention, the term "truncated" with respect to a certain peptide or polypeptide refers to the peptide or polypeptide with one or more amino acids deleted at the N- and/or C-terminus of the parent peptide or polypeptide such as wildtype peptide or polypeptide. According to the invention, a truncated form or variant of an amino acid sequence is a fragment of said amino acid sequence.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods. In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to sequences of peptidases such as DPPIV or LAP, one particular function is one or more peptidase activities displayed by the amino acid sequence from which the fragment or variant is derived. The term "functional fragment" or "functional variant", as used herein, in particular refers to a variant molecule or sequence that comprises an amino acid sequence that is altered by one or more amino acids compared to the amino acid sequence of the parent molecule or sequence and that is still capable of fulfilling one or more of the functions of the parent molecule or sequence, e.g., peptidase activity. In one embodiment, the modifications in the amino acid sequence of the parent molecule or sequence do not significantly affect or alter the characteristics of the molecule or sequence. In different embodiments, the function of the functional fragment or functional variant may be reduced but still significantly present, e.g., peptidase activity of the functional variant may be at least 50%, at least 60%, at least 70%, at least 80%, or at least 90% of the parent molecule or sequence. However, in other embodiments, peptidase activity of the functional fragment or functional variant may be enhanced compared to the parent molecule or sequence.

An amino acid sequence (peptide, protein or polypeptide) "derived from" a designated amino acid sequence (peptide, protein or polypeptide) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the sequences suitable for use herein may be altered such that they vary in sequence from the naturally occurring or native sequences from which they were derived, while retaining the desirable activity of the native sequences.

As used herein, an "instructional material" or "instructions" includes a publication, a recording, a diagram, or any other medium of expression which can be used to communicate the usefulness of the compositions and methods of the invention. The instructional material of the kit of the invention may, for example, be affixed to a container which contains the compositions of the invention or be shipped together with a container which contains the compositions. Alternatively, the instructional material may be shipped separately from the container with the intention that the instructional material and the compositions be used cooperatively by the recipient.

The polypeptides and nucleic acids described herein may be isolated and/or recombinant molecules.

"Isolated" means altered or removed from the natural state. For example, a nucleic acid or a peptide naturally present in a living animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a host cell.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "genetic modification" or simply "modification" includes the transfection of cells with nucleic acid. The term "transfection" relates to the introduction of nucleic acids into a cell. For purposes of the present invention, the term "transfection" also includes the introduction of a nucleic acid into a cell or the uptake of a nucleic acid by such cell. According to the present invention, a cell for transfection of a nucleic acid described herein can be present in vitro. According to the invention, transfection can be transient or stable. For some applications of transfection, it is sufficient if the transfected genetic material is only transiently expressed. RNA can be transfected into cells to transiently express its coded protein. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. Such stable transfection can be achieved by using virus-based systems or transposon-based systems for transfection.

Nucleic Acids

The term "polynucleotide" or "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

In one embodiment, the nucleic acid described herein may have modified and/or non-naturally occurring nucleosides.

Nucleic acids may be comprised in a vector. The term "vector" as used herein refers to a nucleic acid molecule capable of transporting another nucleic acid to which it has been linked and includes any vectors known to the skilled person including plasmid vectors, cosmid vectors, phage vectors such as lambda phage, viral vectors such as retroviral, adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments. "Plasmid" refers to a circular double stranded DNA loop into which additional DNA segments can be ligated. A "viral vector" is a vector wherein additional DNA segments can be ligated into a viral genome.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

"Expression vectors" are capable of directing the expression of genes to which they are operatively linked. In general, expression vectors used in recombinant DNA techniques are often present in the form of plasmids. In the present specification, "plasmid" and "vector" can be used interchangeably as the plasmid is the most commonly used form of vector. However, the invention is intended to include other forms of expression vectors, such as viral vectors (e.g., replication defective retroviruses, adenoviruses and adeno-associated viruses), which serve equivalent functions.

The production of a functional protein is intimately related to the cellular machinery of the organism producing the protein. *E. coli* has typically been the "factory" of choice for the expression of many proteins because its genome has been fully mapped and the organism is easy to handle; grows rapidly; requires an inexpensive, easy-to-prepare medium for growth; and secretes protein into the medium which facilitates recovery of the protein. However, *E. coli* is a prokaryote and lacks intracellular organelles, such as the endoplasmic reticulum and the golgi apparatus that are present in eukaryotes, which contain enzymes which modify the proteins being produced. Many eukaryotic proteins can be produced in *E. coli* but these may be produced in a nonfunctional, unfinished form, since glycosylation or post-translational modifications do not occur.

Therefore, eukaryotic yeast, mammalian and plant expression systems are frequently used for protein production. For example, the methanoltrophic yeast *P. pastoris* has become a powerful host for the heterologous expression of proteins and has been established as an alternative eukaryotic host for the expression of human proteins with high-throughput technologies.

As another example, plants are being used as expression hosts for large-scale heterologous expression of proteins and offer potential advantages of cost-effectiveness, scalability and safety over traditional expression systems. There are currently a variety of plant heterologous expression systems including transient expression, plant cell-suspension cultures, recombinant plant viruses and chloroplast transgenic systems. While proteins expressed in plants have some variations from mammalian proteins (e.g., glycosylation), there is currently no evidence that these differences result in adverse reactions in human patients.

Another suitable heterologous expression system uses insect cells, often in combination with baculovirus expression vectors. Baculovirus vectors are available for expressing proteins in cultured insect cells. One particularly preferred expression system for production of polypeptides described herein is the *Pichia pastoris* expression system. *P. pastoris* has been developed to be an outstanding host for the production of foreign proteins since its alcohol oxidase promoter was isolated and cloned. Compared to other eukaryotic expression systems, *Pichia* offers many advantages, because it does not have the endotoxin problem associated with bacteria nor the viral contamination problem of proteins produced in animal cell cultures. Furthermore, *P. pastoris* can utilize methanol as a carbon source in the absence of glucose. The *P. pastoris* expression system uses the methanol-induced alcohol oxidase (AOX1) promoter, which controls the gene that codes for the expression of alcohol oxidase, the enzyme that catalyzes the first step in the metabolism of methanol. This promoter has been characterized and incorporated into a series of *P. pastoris* expression vectors. Since the proteins produced in *P. pastoris* are typically folded correctly and secreted into the medium, the fermentation of genetically engineered *P. pastoris* provides an excellent alternative to *E. coli* expression systems. Furthermore, *P. pastoris* has the ability to spontaneously glycosylate expressed proteins, which also is an advantage over *E. coli*. A number of proteins have been produced using this system, including tetanus toxin fragment, Bordatella pertussis pertactin, human serum albumin and lysozyme.

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally occurring RNA.

In certain embodiments of the present disclosure, the RNA is messenger RNA (mRNA) that relates to an RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In some embodiments, the RNA according to the present disclosure comprises a 5'-cap. The term "5'-cap" refers to a structure found on the 5'-end of an mRNA molecule and generally consists of a guanosine nucleotide connected to the mRNA via a 5'- to 5'-triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand or may be attached to RNA post-transcriptionally using capping enzymes.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) sequence. Thus, the 3'-UTR is upstream of the poly(A) sequence (if present), e.g. directly adjacent to the poly(A) sequence.

As used herein, the term "poly(A) sequence" or "poly-A tail" refers to a sequence of adenylate residues which is typically located at the 3'-end of an RNA molecule. Poly(A) sequences are known to those of skill in the art and may follow the 3'-UTR in the RNAs described herein. In one embodiment of all aspects of the invention, a nucleic acid described herein is expressed in a cell transfected with the nucleic acid to provide the encoded polypeptide. In one embodiment, expression is into the extracellular space, i.e., the encoded polypeptide is secreted.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

In the context of the present disclosure, the term "transcription" relates to a process, wherein the genetic code in a DNA sequence is transcribed into RNA. Subsequently, the RNA may be translated into peptide or protein.

According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term “expression” as used herein is defined as the transcription and/or translation of a particular nucleotide sequence.

With respect to RNA, the term “expression” or “translation” relates to the process in the ribosomes of a cell by which a strand of mRNA directs the assembly of a sequence of amino acids to make a peptide or protein.

As used herein “endogenous” refers to any material from or produced inside an organism, cell, tissue or system.

As used herein, the term “exogenous” refers to any material introduced from or produced outside an organism, cell, tissue or system.

As used herein, the terms “linked,” “fused”, or “fusion” are used interchangeably. These terms refer to the joining together of two or more elements or components or domains.

Pharmaceutical Compositions

In one embodiment of all aspects of the invention, the components described herein such as polypeptides may be administered in a pharmaceutical composition which may comprise a pharmaceutically acceptable carrier and may optionally comprise stabilizers etc. In one embodiment, the pharmaceutical composition is for therapeutic or prophylactic treatments, e.g., for use in treating or preventing gluten-related disorders.

The term “pharmaceutical composition” relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation.

The pharmaceutical compositions according to the present disclosure are generally applied in a “pharmaceutically effective amount” and in “a pharmaceutically acceptable preparation”.

The term “pharmaceutically acceptable” refers to the non-toxicity of a material which does not interact with the action of the active component of the pharmaceutical composition.

The term “pharmaceutically effective amount” or “therapeutically effective amount” refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term “excipient” as used herein refers to a substance which may be present in a pharmaceutical composition of the present disclosure but is not an active ingredient. Examples of excipients include without limitation, carriers, binders, diluents, lubricants, thickeners, surface active agents, preservatives, stabilizers, emulsifiers, buffers, flavoring agents, or colorants.

The term “diluent” relates a diluting and/or thinning agent. Moreover, the term “diluent” includes any one or more of fluid, liquid or solid suspension and/or mixing media. Examples of suitable diluents include ethanol, glycerol and water.

The term “carrier” refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carriers include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

In one embodiment, pharmaceutical compositions described herein may be administered orally, intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, “parenteral administration” refers to the administration in any manner other than through the gastrointestinal tract, such as by intravenous injection. In a preferred embodiment, the pharmaceutical composition is formulated for oral administration.

The term “co-administering” as used herein means a process whereby different compounds or compositions are administered to the same patient. The different compounds or compositions may be administered simultaneously, at essentially the same time, or sequentially.

Treatments

The present invention provides methods and agents for treating a pathological state in a subject such as gluten-related disorders (including celiac disease and non-celiac gluten sensitivity), digestive tract malabsorption, sprue, an allergic reaction and an enzyme deficiency. For example, the allergic reaction can be a reaction to gluten. The present invention, in particular, provides methods and agents for treating celiac disease (CeD) and non-celiac gluten sensitivity. Methods described herein may comprise administering an effective amount of a polypeptide or composition described herein.

A cocktail of ruLAPII and ruDPPIV degrades gluten-immunogenic peptides (GIP) in-situ, as they are generated in the digest of gluten in a matter of a few minutes to non-immunogenic single amino acids and dipeptides, thereby preventing the immune response and the subsequent symptoms of gluten-related disorders. Since the truncated polypeptide variants described herein retain biological activity, they have the same or a similar usefulness as the parent polypeptides from which they are derived.

The therapeutic compounds or compositions of the invention may be administered prophylactically (i.e., to prevent a disease or disorder) or therapeutically (i.e., to treat a disease or disorder) to subjects suffering from, or at risk of (or susceptible to) developing a disease or disorder. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity, which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In some embodiments, administration of an agent or composition of the present invention may be performed by single administration or boosted by multiple administrations.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, clinical entities, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

The term "gluten-related disorders" relates to conditions and diseases caused by the ingestion of gluten-containing food, such as wheat-based food. The term includes celiac disease (CeD), wheat allergy (WA) and non-celiac gluten sensitivity (NCGS) as well as other diseases that may profit from a gluten-free diet (GFD).

Celiac disease (CeD) is a chronic immune-mediated enteropathy precipitated by gluten-immunogenic peptides (GIP) in genetically predisposed individuals. GIP are generated in the digest of gluten and play a central role in the disease pathology; they consist of digestion-resistant proline-rich peptides, which act as T-cell epitopes in HLA-DQ2 and HLA-DQ8 positive patients, whereby CD4+ T-cells associate with HLA-molecules and initiate a typical autoimmune pathology, which explains the clinical symptomatology and long-term complications. Current diagnosis is based on the presence of clinical symptoms of enteropathy, villous atrophy, crypt hyperplasia and intraepithelial lymphocytosis, and the presence of circulating CeD-specific antibodies to tissue transglutaminase (tTG), deamidated gliadin peptides (DGP), and endomysium (EMA) in the small intestine.

Non-celiac gluten sensitivity is a gluten-related disorder related to the ingestion of gluten. In contrast to CeD no specific genetic predisposition factor for NCGS has been identified so far and serological biomarkers are not available for NCGS, since the determination of celiac-related antibodies is not sensitive or specific to NCGS. The NCGS patients' gastrointestinal tracts and their intestinal permeability are normal and the lesions in the histological picture of their duodenal mucosa are minor, but increased infiltration of eosinophils and basophils to the duodenal lamina propria and activation of circulating basophils have been observed in NCGS patients which may be responsible for syndrome-related symptoms.

Since gluten-derived GIP are the causative trigger of gluten-related disorders, a strict lifelong gluten-free diet has been the mainstay of treatment. However, a gluten-free diet is very difficult to achieve in day-to-day life.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder but may or may not have the disease or disorder. In many embodiments, the individual is a human being. Unless otherwise stated, the terms “individual” and “subject” do not denote a particular age, and thus encompass adults, elderlies, children, and newborns. In embodiments of the present disclosure, the “individual” or “subject” is a “patient”.

The term “patient” means an individual or subject for treatment, in particular a diseased individual or subject.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown but are to be accorded the scope consistent with the claims.

EXAMPLES

The following examples describe screening work that was performed to test the production of a short variant of ruLAPII (ruLAPII_short) and ruDPPIV (ruDPPIV_short) in Lonza’s *P. pastoris* expression platform. These variants of ruLAPII and ruDPPIV were purified and tested for enzymatic activity (U/mg purified protein) together with their full-length variant. The purified shortened variants were analyzed by intact molecule mass spectroscopy.

ruDPPIV_short

23 PAOX1 clones in the strain background LP1 were analyzed for secretion of ruDPPIV_short into the culture medium using SDS PAGE/Coomassie stain and enzymatic activity (AMC assay; SOP provided by Amyra). Several promising clones were identified with an enzymatic activity of up to 2'032 U/L [Reference strain LP1 (pCKP6003.1) =4'325 U/L] and a lower product titer than the reference strain. Five clones were tested together with the reference strain in high cell density fermentation (Ambr250). The enzymatic activity was up to 9'056 U/L [Reference strain LP1 (pCKP6003.1)=21'586 U/L] and a lower product titer than the reference strain. The product ruDPPIV [expressed in strain LP1 (pCKP6003.1)] and ruDPPIV_short [expressed in strain LP1 (pFJP6015.6)] were purified from the culture supernatant and the activity was measured. Similar specific productivities were measured.

ruDPPIV_short: 12.7 U/mg ruDPPIV full length: 12.4 U/mg

The purified ruDPPIV and ruDPPIV_short were deglygosylated and analyzed for possible degradation via mass spectroscopy.

ruDPPIV_short: full-length product and degradation products observed ruDPPIV full-length: degradation products only observed ruLAPII_short 23 PAOX1 clones in the strain background LP1 were analyzed for secretion of ruLAPII_short into the culture medium using SDS PAGE/Coomassie stain and enzymatic activity (AMC assay; SOP provided by Amyra). Several promising clones were identified with an enzymatic activity of up to 26 U/L [Reference strain LP1 (pCKP6011.4)=174 U/L] and lower product titer than the reference strain. Five clones were tested together with the reference strain in high cell density fermentation (Ambr250). The enzymatic activity was up to 371 U/L [Reference strain LP1 (pCKP6011.4)= 1'212 U/L]. The product ruLAPII [expressed in strain LP1 (pCKP6011.4)] and ruLAPII_short [expressed in strain LP1 (pFJP6014.13)] were purified from the culture supernatant and the activity was measured. The specific activity of the short variant was slightly lower than the specific activity of wildtype ruLAPII.

ruLAPII_short: 1.1 U/mg ruLAPII full-length: 1.5 U/mg

The purified ruLAPII and ruLAPII_short were deglygosylated and analyzed for possible degradation via mass spectroscopy.

ruLAPII_short: only full-length product, no degradation products observed ruLAPII full-length: degradation products only observed

Example 1: Materials and Methods

1. Strains and Plasmids 1.1 *Escherichia coli* Strains

DH10B (Invitrogen, Cat. No. 18297-00) was used for all cloning steps.

1.2 *Pichia pastoris* Strains

All *P. pastoris* expression studies were done with strain LP1. Genotype description can be shared upon request.

1.3 Plasmids

The PAOX1 plasmid pFJP6014 was constructed by ligation of the linear ~3085 bp SbfI/SfiI fragment of pXSP603 vector with the linear 1480 bp SbfI/SfiI digested fragment (containing the short ruLAPII variant) from ATUM400860.

The PAOX1 plasmid pFJP6015 was constructed by ligation of the linear ~3085 bp SbfI/SfiI fragment of pXSP603 vector with the linear 2314 bp SbfI/SfiI digested fragment (containing the short ruDPPIV variant) from ATUM400861.

Subsequently, chemically competent DH10B cells were transformed with the ligation mix. After restriction digest analysis, the gene of interest in the newly generated plasmids was confirmed by sequencing and the strain LP1 was transformed with the plasmid pFJP6014 and pFJP6015 for subsequent multi copy screening.

TABLE 1

Overview of *P. pastoris* plasmids. All plasmids contain the same vector backbone and a Zeocin ™ resistance marker.

| Plasmid ID | Promoter | Signal peptide | Product |
|---|---|---|---|
| pFJP6014 | PAOX1 | SP_long | ruLAPII_short |
| pFJP6015 | PAOX1 | SP_short | ruDPPIV_short |

2. Genes

The DNA sequence of the ruLAPII_short product derived from the original ruLAPII sequence (i.e. plasmid pCKP6011) except the missing codons at the 5' and 3' side (see section 3.1 and 3.2).

The DNA sequence of the ruDPPIV_short product derived from the original ruDPPIV sequence (i.e. plasmid pCKP6003) except the missing codons at the 5' and 3' side (see section 3.3 and 3.4).

3. Protein Sequences 3.1 ruLAPII

Italic indicates missing amino acids in the corresponding short variant.

(SEQ ID NO: 2)
*HPVVGQ*EPFGWPFKPMVTQDDLQNKIKLKDIMAGVEKLQSFSDAHPEKN
RVFGGNGHKDTVEWIYNEIKATGYYDVKKQEQVHLWSHAEAALNANGKD
LKASAMSYSPPASKIMAELVVAKNNGCNATDYPANTQGKIVLVERGVCS
FGEKSAQAGDAKAAGAIVYNNVPGSLAGTLGGLDKRHVPTAGLSQEDGK
NLATLVASGKIDVTMNVISLFENRTTWNVIAETKGGDHNNVIMLGAHSD
SVDAGPGINDNGSGSIGIMTVAKALTNFKLNNAVRFAWWTAEEFGLLGS
TFYVNSLDDRELHKVKLYLNFDMIGSPNFANQIYDGDGSAYNMTGPAGS
AEIEYLFEKFFDDQGIPHQPTAFTGRSDYSAFIKRNVPAGGLFTGAEVV
KTPEQVKLFGGEAGVAYDKNYHRKGDTVANINKGAIFLNTRAIAYAIAE
YARSLKGFPTRPKTGK*RDVNPQYSKMPGGGCGHHTVFM*

Theoretical Mw: 51843.34 Theoretical pI: 6.73

3.2 ruLAPII short variant (SEQ ID NO: 4)
EPFGWPFKPMVTQDDLQNKIKLKDIMAGVEKLQSFSDAHPEKNRVFGGN
GHKDTVEWIYNEIKATGYYDVKKQEQVHLWSHAEAALNANGKDLKASAM
SYSPPASKIMAELVVAKNNGCNATDYPANTQGKIVLVERGVCSFGEKSA
QAGDAKAAGAIVYNNVPGSLAGTLGGLDKRHVPTAGLSQEDGKNLATLV
ASGKIDVTMNVISLFENRTTWNVIAETKGGDHNNVIMLGAHSDSVDAGP
GINDNGSGSIGIMTVAKALTNFKLNNAVRFAWWTAEEFGLLGSTFYVNS
LDDRELHKVKLYLNFDMIGSPNFANQIYDGDGSAYNMTGPAGSAEIEYL
FEKFFDDQGIPHQPTAFTGRSDYSAFIKRNVPAGGLFTGAEVVKTPEQV
KLFGGEAGVAYDKNYHRKGDTVANINKGAIFLNTRAIAYAIAEYARSLK
GFPTRPKTGK Theoretical Mw: 48695.79 Theoretical pI: 6.62

3.3 ruDPPIV

Italic indicates missing amino acids in the corresponding short variant.

(SEQ ID NO: 1)
*I*VPPREPRSPTGGGNKLLTYKECVPRATISPRSTSLAWINSEEDGRYIS
QSDDGALILQNIVTNTNKTLVAADKVPKGYYDYWFKPDLSAVLWATNYT
KQYRHSYFANYFILDIKKGSLTPLAQDQAGDIQYAQWSPMNNSIAYVRG
NDLYIWNNGKTKRITENGGPDIFNGVPDWVYEEEIFGDRFALWFSPDGE
YLAYLRFNETGVPTYTIPYYKNKQKIAPAYPRELEIRYPKVSAKNPTVQ
FHLLNIASSQETTIPVTAFPENDLVIGEVAWLSSGHDSVAYRAFNRVQD
REKIVSVKVESKESKVIRERDGTDGWIDNLLSMSYIGNVNGKEYYVDIS
DASGWAHIYLYPVDGGKEIALTKGEWEVVAILKVDTKKKLIYFTSTKYH
STTRHVYSVSYDTKVMTPLVNDKEAAYYTASFSAKGGYYILSYQGPNVP
YQELYSTKDSKKPLKTITSNDALLEKLKEYKLPKVSFFEIKLPSGETLN
VKQRLPPNFNPHKKYPVLFTPYGGPGAQEVSQAWNSLDFKSYITSDPEL
EYVTWTVDNRGTGYKGRKFRSAVAKRLGFLEAQDQVFAAKEVLKNRWAD
KDHIGIWGWSYGGFLTAKTLETDSGVFTFGISTAPVSDFRLYDSMYTER

-continued

YMKTVELNADGYSETAVHKVDGFKNLKGHYLIQHGTGDDNVHFQNAAVL
SNTLMNGGVTADKLTTQWFTDSDHGIRYDMDSTYQYKQLSKMVYDQKQR
RPESPPMHQW*SKRVLAALFGERAEE*

Theoretical Mw: 86486.34 Theoretical pI: 8.05

3.4 ruDPPIV short variant (SEQ ID NO: 3)
VPPREPRSPTGGGNKLLTYKECVPRATISPRSTSLAWINSEEDGRYISQ
SDDGALILQNIVTNTNKTLVAADKVPKGYYDYWFKPDLSAVLWATNYTK
QYRHSYFANYFILDIKKGSLTPLAQDQAGDIQYAQWSPMNNSIAYVRGN
DLYIWNNGKTKRITENGGPDIFNGVPDWVYEEEIFGDRFALWFSPDGEY
LAYLRFNETGVPTYTIPYYKNKQKIAPAYPRELEIRYPKVSAKNPTVQF
HLLNIASSQETTIPVTAFPENDLVIGEVAWLSSGHDSVAYRAFNRVQDR
EKIVSVKVESKESKVIRERDGTDGWIDNLLSMSYIGNVNGKEYYVDISD
ASGWAHIYLYPVDGGKEIALTKGEWEVVAILKVDTKKKLIYFTSTKYHS
TTRHVYSVSYDTKVMTPLVNDKEAAYYTASFSAKGGYYILSYQGPNVPY
QELYSTKDSKKPLKTITSNDALLEKLKEYKLPKVSFFEIKLPSGETLNV
KQRLPPNFNPHKKYPVLFTPYGGPGAQEVSQAWNSLDFKSYITSDPELE
YVTWTVDNRGTGYKGRKFRSAVAKRLGFLEAQDQVFAAKEVLKNRWADK
DHIGIWGWSYGGFLTAKTLETDSGVFTFGISTAPVSDFRLYDSMYTERY
MKTVELNADGYSETAVHKVDGFKNLKGHYLIQHGTGDDNVHFQNAAVLS
NTLMNGGVTADKLTTQWFTDSDHGIRYDMDSTYQYKQLSKMVYDQKQRR
PESPPMHQWS Theoretical Mw: 84931.48 Theoretical pI: 7.77

4. Primary Screening 4.1 Multi Copy Screening

After linearization of the plasmids with DraI, the strain LP1 was transformed with the plasmid pFJP6014 (ruLAPII_short) and pFJP6015 (ruDPPIV_short) and plated out onto agar plates containing different concentrations of Zeocin™ (Invitrogen, Cat. No. ant-zn-1) (500 and 1000 μg/mL). After incubation at 30° C. for 48 hrs, 23 clones per host/plasmid integration were picked and streaked out onto master plates (containing 100 μg/ml Zeocin™) for subsequent expression screening in 24 well plates.

4.2 Expression in 24 Well Plates

Expression experiments were done in 24 well plates (GE Healthcare Life sciences; Cat. No. 7701-5102) containing YPC (Yeast extract, peptone, 100 mM Sodium Citrate, pH 6.0) medium supplemented with concentrated polysaccharide (50 g/L, EnPump200, EnPresso, Germany) and 14 U/L concentrated enzyme mix (EnPump200, EnPresso, Germany). The main cultures (2 mL) were inoculated to a start OD600 of 2 with overnight cultures grown at 30° C. in YPG (Yeast Peptone Glycerol). Subsequently, the cultures were incubated at 25° C. and 260 rpm shaking and induced by repeated Methanol shots (1%) every 12 hours for 72 hrs.

5. High Cell Density Fermentation

The media are based on a medium, modified from Gasser (Gasser et al. 2013; Future Microbiol., 8 (2): 191-208) and Prielhofer (Prielhofer et al. 2013, Microbial Cell Factories 12:5), containing 3 g kg-1 peptone (Biokar, Cat. No. A1601). Reagents and solutions are stored at room temperature, except for PTM1, stored at 4° C. under dark conditions, Biotin stored at −4° C., and Biotin solution stored at 4° C. Except otherwise stated the reagents were supplied by Merck (Darmstadt, Germany).

5.1 Preculture

In order to produce the inoculum for the main fermentation, cultivations in shake flasks were performed. For each strain 100 ml of the preculture medium were filled into a 500 mL baffled shake flask and inoculated with 1 ml of a −80° C. glycerol stock culture. The shake flasks were incubated for 21 h (±2 h) at 170 rpm (Ø 25 mm) and 30° C. on an orbital shaker (Kühner ISF-1-W). The axenic state of the culture was confirmed by microscopy (Nikon Eclipse) just before transferring the inoculum to the bioreactor. The main fermentations were started from these precultures by inoculating the fermenters to an initial optical density of 1.

5.2 Main Fermentation

After preparing the periphery, media and solutions, the bioreactors were filled with 90 mL of batch medium, autoclaved at 121° C. for 30 min and then installed at the Ambr250 station. The feed system for the addition of carbon substrate and base was cleaned in place by rinsing with 70% ethanol, 2 M sodium hydroxide and then demineralized water for 30 min each. For pH control of the PAOX1 strains, acid (phosphoric acid) and base (ammonia) were used. The set-points for agitation and aeration with air and oxygen are determined by a cascade controller, which works in such a way that the value for dissolved oxygen remains between 25% and 40%.

5.3 Setup and Strategy of the Fermentations

The initial optical density of ~1 and the glycerol concentration predetermine the duration of the batch phase (length of batch phase).

ruLAPII_short

The fermentation was done according to Lonza SOP143961-2 and report 2014.157 (S. Bieli and N. Krumov, 2014).

Figure 2:
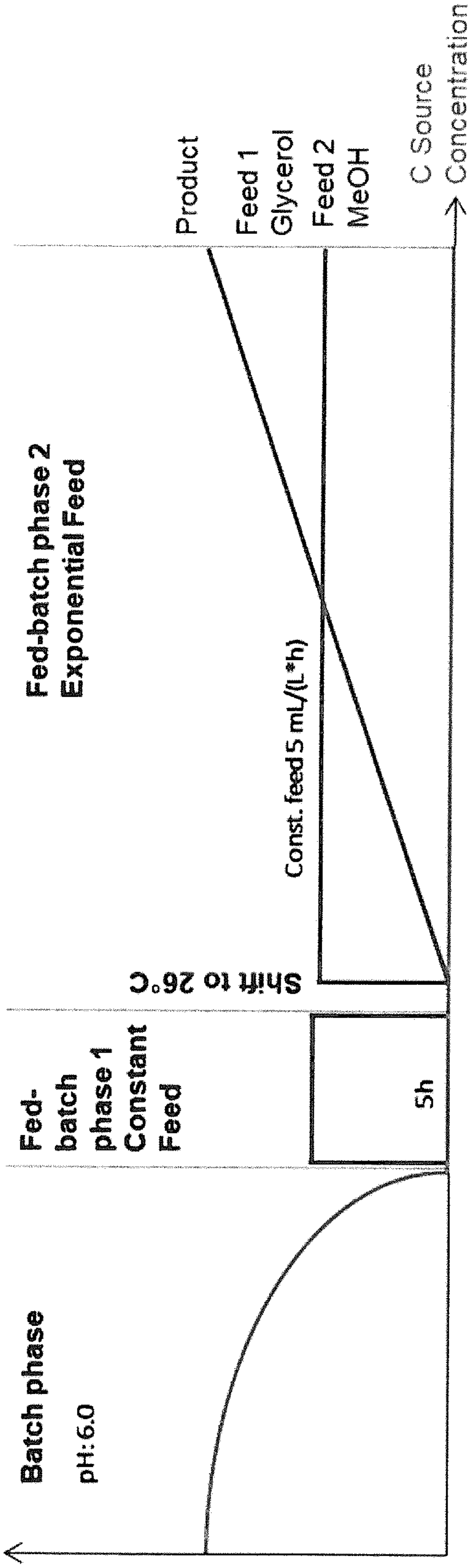
FIG. 2. Feeding strategy for ruLAPII_short.

After the batch phase, the main fermentation is divided into a phase of biomass generation followed by a phase of target protein production (see FIG. 2). A constant glycerol feed (45%) of 12 mL·L$^{-1}$ BV h$^{-1}$ for 5 hours is performed during fed-batch phase 1. This phase is followed by a short starvation period of about 30 minutes where no feed is introduced to the fermenters, targeting on one hand the complete glycerol depletion, and on the other hand the adaptation of the cell metabolism for the pending methanol feeding. The production phase begins with a temperature shift from 30° C. to 26° C. and the start of the constant methanol feed of 5 mL·L$^{-1}$ BV h$^{-1}$.

ruDPPIV_short

The fermentation was done according to Lonza SOP143601-2 and report 2014.157 (S. Bieli and N. Krumov, 2014).

Figure 3:
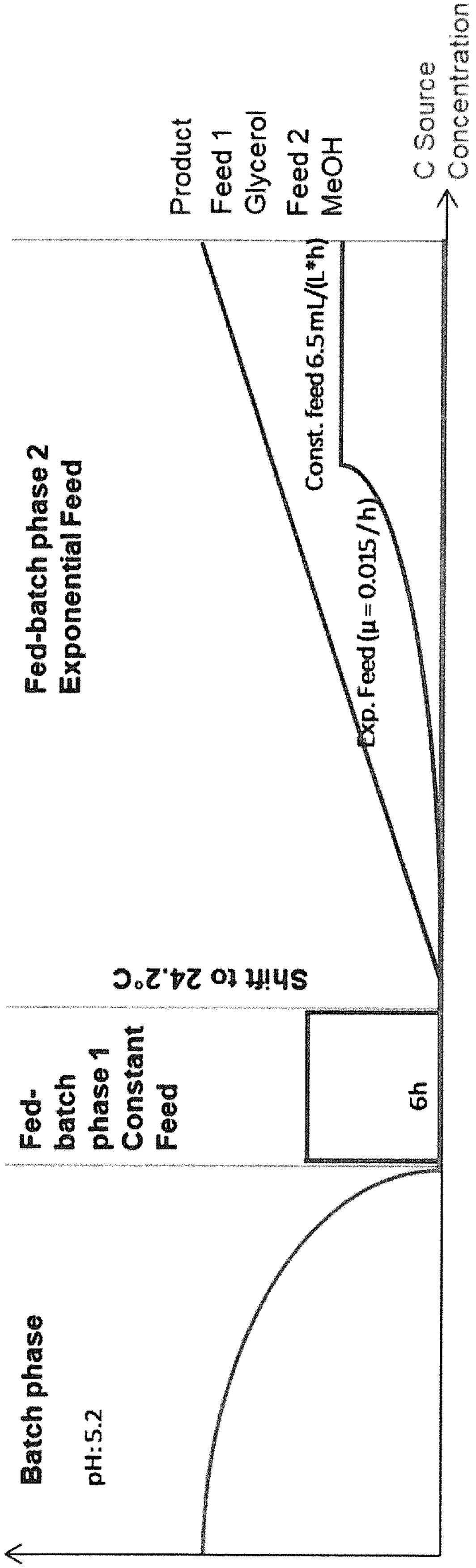
FIG. 3. Feeding strategy for ruDPPIV_short.

After the batch phase (pH of 5.2), the main fermentation is divided into a phase of biomass generation followed by a phase of target protein production (see FIG. 3). A constant glycerol feed (45%) of 12 mL·L$^{-1}$ BV h$^{-1}$ for 6 hours is performed during fed-batch phase 1. This phase is followed by a short starvation period of about 30 minutes where no feed is introduced to the fermenters, targeting on one hand the complete glycerol depletion, and on the other hand the adaptation of the cell metabolism for the pending methanol feeding. The production phase begins with a temperature shift from 30° C. to 24.2° C. and the start of the exponential methanol feed until a feed rate of 6.5 mL·L$^{-1}$ BV h$^{-1}$ is reached and continued until the end of fermentation.

Fermentations with the Ambr250 system were executed by using a custom programming script allowing an automatic start of the different feeds (by detection of the DO-spike at the end of the batch phase) and programmed duration of the different feeding phases. The fermentation parameters were controlled and recorded by the IRIS process control system.

6. Downstream Purification

Purification was done using a simplified batch mode based on the presentation “GLH-003: DPP4 and LAP2 step elution feasibility” (Presentation; A. Zurbriggen et al., 2016) and the block flow diagrams of demonstration runs.

ruLAPII_short

Purification was adapted for batch mode according to “LAP2_BFD_Demonstration Runs_01” (A. Zurbriggen, 2016). After fermentation and centrifugation of the culture broth for 45 min at 4000 rpm, 4° C., 100 μL Halt Protease Inhibitor-Single-Use Cocktail (100×) (Thermo Scientific, Cat. No. 78430) was added to 12 mL EOF culture supernatant.

Resin preparation 1 mL SP Sepharose® XL (GE Healthcare, Cat. No. GE17-5073-01, binding capacity 5-10 mg/ml) was added to a 15 mL Falcon tube and mixed. Subsequently, the Falcon tube was centrifuged for 5 min at 1000 rpm. The resin wash washed with 10 mL MQ water and centrifuged for 5 min at 1000 rpm. Subsequently, the supernatant was removed by pipetting and 10 mL 50 mM Na-Acetate, pH 5.0 was added for equilibration. After centrifugation for 5 min at 1000 rpm, the supernatant of the resin was removed by pipetting and the resin washed again with 10 ml 50 mM Na-Acetate, pH 5.0.

Sample Incubation

After centrifugation for 5 min at 1000 rpm, the supernatant of the resin was removed by pipetting and the resin was incubated with 12 mL EOF culture supernatant for 30 minutes at room temperature on a rocking shaker. After incubation, the Falcon tube was centrifuged for 5 min at 1000 rpm and the supernatant removed by pipetting.

Wash

The resin was washed with 10 ml 20 mM Na-Phosphate, pH 6.0, centrifuged for 5 min at 1000 rpm and the supernatant removed by pipetting. After wash, the Falcon tube was centrifuged for 5 min at 1000 rpm and the supernatant removed by pipetting.

Elution 2 mL 20 mM Na-Phosphate, pH 6.0, 130 mM NaCl was added to the resin and incubated for 10 min at room temperature on a rocking shaker. Subsequently, the Falcon tube was centrifuged for 5 min at 1000 rpm and the supernatant was isolated and stored at −20° C. for subsequent analytics.

ruDPPIV_short

Purification was adapted for batch mode according to “DPP4_BFD_Demonstration Runs_01” (A. Zurbriggen, 2016). After fermentation and centrifugation of the culture broth for 45 min at 4000 rpm, 4° C., 100 μL Halt Protease Inhibitor-Single-Use Cocktail (100×) (Thermo Scientific, Cat. No. 78430) was added to 12 mL EOF culture supernatant.

Resin preparation 1 mL SP Sepharose® XL (GE Healthcare, Cat. No. GE17-5073-01), binding capacity 5-10 mg/mL, was added to a 15 mL Falcon tube and mixed. Subsequently, the Falcon tube was centrifuged for 5 min at 1000 rpm. The resin wash washed with 10 mL MQ water and centrifuged for 5 min at 1000 rpm and the supernatant was removed by pipetting and 10 ml 25 mM Tris, pH 7.2 was added for equilibration. After centrifugation for 5 min at 1000 rpm, the supernatant of the resin was removed by pipetting and the resin washed again with 10 mL 25 mM Tris, pH 7.2.

Sample Incubation

After centrifugation for 5 min at 1000 rpm, the supernatant of the resin was removed by pipetting and the resin was incubated with 12 mL EOF culture supernatant for 30 minutes at room temperature on a rocking shaker. After incubation, the Falcon tube was centrifuged for 5 min at 1000 rpm and the supernatant removed by pipetting.

Wash

The resin was washed with 10 mL 25 mM Tris, pH 7.2, 20 mM NaCl, centrifuged for 5 min at 1000 rpm and the supernatant removed by pipetting. After wash, the Falcon tube was centrifuged for 5 min at 1000 rpm and the supernatant removed by pipetting.

Elution 2 mL 25 mM Tris, pH 7.2, 130 mM NaCl was added to the resin and incubated for 10 min at room temperature on a rocking shaker. Subsequently, the Falcon tube was centrifuged for 5 min at 1000 rpm and the supernatant was isolated and stored at −20° C. for subsequent analytics.

7. Analytical Methods 7.1 Sample Treatment

Cells (1 ml samples) were removed by centrifugation at 6000 g for 5 min at 4° C. and the supernatant was collected. The samples were either directly subjected to analysis or stored at −80° C. for later testing.

7.2 Wet Cell Weight

In order to measure the wet cell weight, 1 mL of the fermentation suspension were transferred into pre-weighed tubes. The samples were centrifuged at 15'000 g for 15 min and the supernatant isolated. Afterwards, the tube was weighed and the wet cell weight in g $L^{-1}$ (biomass per current fermentation volume) calculated.

7.3 Dry Cell Weight

For dry cell weight determination, samples of 1 ml were centrifuged for 15 min at 17'000 g (4° C.). The supernatant was discarded, and the resulting pellet was dried at 100° C. for 48 h. The resulting dry cell weight in g $L^{-1}$ (biomass per current fermentation volume) was calculated.

7.4 Optical Density

Biomass concentration was determined by measuring the optical density at 600 nm in the linear range (between OD600=0.05 and OD=0.5) of a photo spectrometer. In brief, 10 µl of culture were added to 96 well plates (VWR, Cat. No 732-2746) and diluted in PBS (190 µL) using a Starlet liquid handler (Hamilton, Bonaduz, Switzerland) (dilution factor 1:20). Subsequently, optical density at 600 nm was measured with a Tecan Infinite reader. As blank, 200 µL YPC media was used.

7.5 Detection of Product by SDS PAGE/Coomassie Stain

The SDS-PAGE was run under reducing conditions. Precasted Criterion 12% Bis-Tris SDS gels (Bio-Rad, Cat. No. 567-1124) were used with MES buffer (Bio-Rad, Cat. No. 161-0796). Samples were mixed with NuPAGE 4× LDS loading buffer (Invitrogen, Cat. No. NP0007) and incubated for 5 min at 95° C. Per lane, 7.5 µL sample (10 µL culture supernatant, plus 5 µL 4× LDS loading buffer) was loaded. As a molecular weight standard, Mark12 (Invitrogen, Cat. No. LC5677) was loaded. As reference, 1 µg recombinant ruLAPII (Biomeva LAP-2 100.6 mg/ml) or was loaded. Electrophoresis was done for approximately 80 min at 200 V. The separated proteins were visualized by staining with GelCode Blue Stain Reagent (Thermo Scientific, Cat. No. 24592) for 1-2 hrs and destained with water over night.

7.6 AMC Activity Assay

Testing of activity was performed in 96 well plate (GreinerOne, Cat. No. 655900). As substrate, 10 mM Gly-Pro-AMC (Bachem, Cat. No. 11225) for ruDPPIV or 10 mM Leu-AMC hydrochloride (Bachem, Cat. No. 11245) for ruLAPII was used. As reaction buffer, 50 mM Tris-HCl buffer (pH 7.5, 1 mM CoCl2; 1% BSA) was used. As standard, 1 mM AMC (solubilized in EtOH, Bachem, Cat. No. Q-1025) was used in a final concentration of 0 nM to 10'000 nM diluted in reaction buffer. The samples (cell free medium) were diluted between 1/400 to 1/2500, so that the fluorescence was within the AMC standard curve. Briefly, 10 µl sample was added together with 10 µL substrate (final concentration: 1 mM) to 90 µl reaction buffer. Measurements were done with the following settings:

Temp: 25° C.

Excitation: 370 nm

Emission: 460 nm

Reaction duration: 30 min

Measurement interval: 30 sec 7.7 BCA Assay (Protein Concentration)

Protein measurement was done according to the manufacturer (Pierce BCA Protein Assay Kit, Cat. No. 23227) adapted for 96-well microtiter plates.

7.8 PNGase Digest (Deglycosylation)

Deglycosylation was done according to the manufacturer (NEB Rapid PNGase F; Cat. No. P0710S). Briefly, 15 µL of elution samples were added to 5 µL Rapid PNGase F Buffer (5×) and incubated at 80° C. for 2 min. After cooling down, 1 µL Rapid PNGase F was added and incubated at 50° C. for 10 min.

7.9 Desalting of Samples

Briefly, desalting was done according to the manufacturer (Merck, Cat. No. UFC503096) for Amicon Ultra-0.5 mL, 30 K. Briefly, five PNGase F digested samples were pooled (total 100 µL) and filled up to 500 µL with 25 mM Tris, pH 7.2. Subsequently, the tube was centrifuged at 14'000 g for 10 min at 4° C. The supernatant was isolated. Then, 20 µL 25 mM Tris, pH 7.2 were added to the filter and centrifuged at 14'000 g for 10 min at 4° C. Both samples were pooled for subsequent analytics.

7.10 Mass Spectroscopy

Analytics was done at B-Fabric (Functional Genomics Center Zurich). Briefly, Prior ESI-MS analyses, samples were desalted using C4 Zip Tips (Millipore, USA) and analyzed in MeOH: 2-PrOH: 0.2% FA (30:20:50). The solution was infused through a fused silica capillary (ID75 µm) at a flow rate of 1 µL/min and sprayed through a PicoTips (ID30 µm). The last were obtained from New Objective (Woburn, MA). Nano ESI-MS analyses of the samples were performed on a Synapt G2_Si mass spectrometer and the data were recorded with the MassLynx 4.2 Software (both Waters, UK). Mass spectra were acquired in the positive-ion mode by scanning an m/z range from 100 to 5000 da with a scan duration of 1 s and an interscan delay of 0.1 s. The spray voltage was set to 3 kV, the cone voltage to 50V, and source temperature 80° C. All four samples were also analyzed by MALDI-MS without any additional sample preparation, i.e. merely applied onto the steel target.

7.11 Glycerol Stock Culture

The −80° C. stock culture used for experiments in the secondary screening was prepared according to the following protocol:

Inoculation of main culture:

Transfer 20 mL YPD medium into 100 ml shake flask

Add 20 µL Zeocin™ (InvivoGen; CatNo. ant-zn-1) (100 mg/mL); final concentration: 100 µg/mL Inoculate with a loop of colonies from plate
Incubate at 30° C., 200 rpm for approximately 20 hrs
Preparation of main culture for storage at −80° C.:
Measure the optical density (OD600), expected OD600 is 40-50
Add 850 μL cultures to Nunc 1.8 mL Cryo tubes containing 150 μl glycerol (100%)
Mix by inverting
Store at −80° C.

Example 2: Primary Screening

After transformation of the *P. pastoris* strains with the linearized plasmid pFJP6015 (ruDPPIV_short) and pFJP6014 (ruLAPII_short), colonies were picked and inoculated in 24 well plates containing 2 mL YPC medium. Only colonies were taken which were clearly separated. In total, 46 clones (23 clones per product) were incubated at 25° C., 260 rpm, grown at pH 6.0 and induced by repeated shots of Methanol (1%) every 12 hrs for 72 hrs. As reference, the precursor strains LP1 (pCKP6003.1, ruDPPIV) and LP1 (pCKP6011.4, ruLAPII) was included. Subsequently, the culture supernatant of the clones was analysed via SDS PAGE/Coomassie stain and enzymatic activity (AMC assay).

1. ruDPPIV_short Variant

The culture supernatant of all LP1 (pCKP6015) clones grown at pH 6.0 were loaded onto a 12% SDS PAGE gel under reducing conditions. As reference, the culture supernatant of the reference strain LP1 (pCKP6003.1, ruDPPIV) was loaded (FIG. 4, lane 26).

Figure 4:
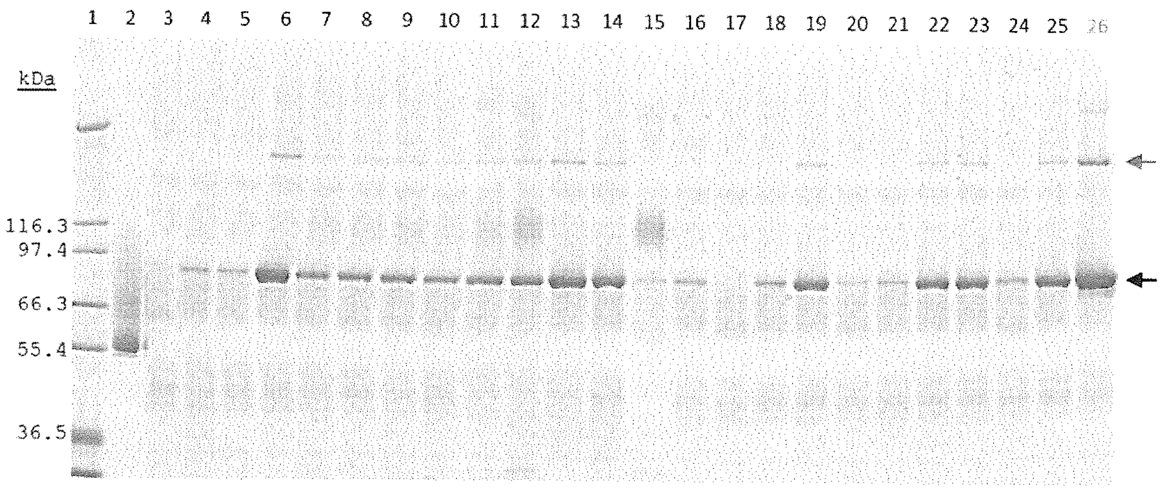
FIG. 4. Coomassie stain of culture supernatant isolated from clones with LP1 (pFJP6015, ruDPPIV_short) strain background. 7.5 μL of culture supernatant were loaded onto a 12% Bis-Tris SDS gel, 26-Well, MES buffer under reducing conditions. A) SDS PAGE/Coomassie stain, Black arrow indicates the position of the ruDPPIV product, Blue arrow indicates the position of a higher molecular weight variant of ruDPPIV.; B) Loading scheme, Black: clones chosen for later high cell density fermentation, Green: reference strain.

As shown in FIG. 4A, the culture supernatant of several clones did show a band running at the same height as the reference strain LP1 (pCKP6003.1) (FIG. 4, lane 26). Strong ruDPPIV_short product could be found in the culture supernatant of clone LP1 (pCKP6015.8) (FIG. 4, lane 6), LP1 (pCKP6015.6) (FIG. 4, lane 13), LP1 (pCKP6015.12) (FIG. 4, lane 14), LP1 (pCKP6015.15) (FIG. 4, lane 19) and LP1 (pCKP6015.18) (FIG. 4, lane 25). For clones with the strongest product band, aggregate formation was observed similar to the results found in the reference strain LP1 (pCKP6003.1) (FIG. 4, compare lane 6, 13, 14, 19 and 25 with lane 26), indicating that the short variants are capable to form aggregates (most likely ruDPPIV dimers) similar to the full length ruDPPIV. The strongest product amount was found in clone LP1 (pFJP6015.8) which was determined visually to be approximately half of the product amount found in the reference strain LP1 (pCKP6003.1).

The culture supernatant of all clones was analyzed for enzymatic activity using the AMC assay (See Example 1, section 7.6). As expected, the culture supernatant of clones showing the highest product titer also showed the highest enzymatic activity. The highest activity was found in the culture supernatant of clone LP1 (pFJP6015.8) (2032 U/L) which was approximately half of the activity measured in the reference strain LP1 (pCKP6003.1) (4325 U/L). The reference clone LP1 (pCKP6003.1) showed reproducible activity as in the initial screening (3977 U/L, ResRep 2014.111). In summary, the data suggested that the short variant of ruDPPIV were still enzymatically active.

2. ruLAPII_short Variant

The culture supernatant of all LP1 (pCKP6014) clones grown at pH 6.0 were loaded onto a 12% SDS PAGE gel under reducing conditions. As reference, the culture supernatant of the reference strain LP1 (pCKP6011.4, ruLAPII) (FIG. 5, lane 26) and purified ruLAPII (Biomeva LAP-2 100.6 mg/mL) was loaded.

Figure 5:
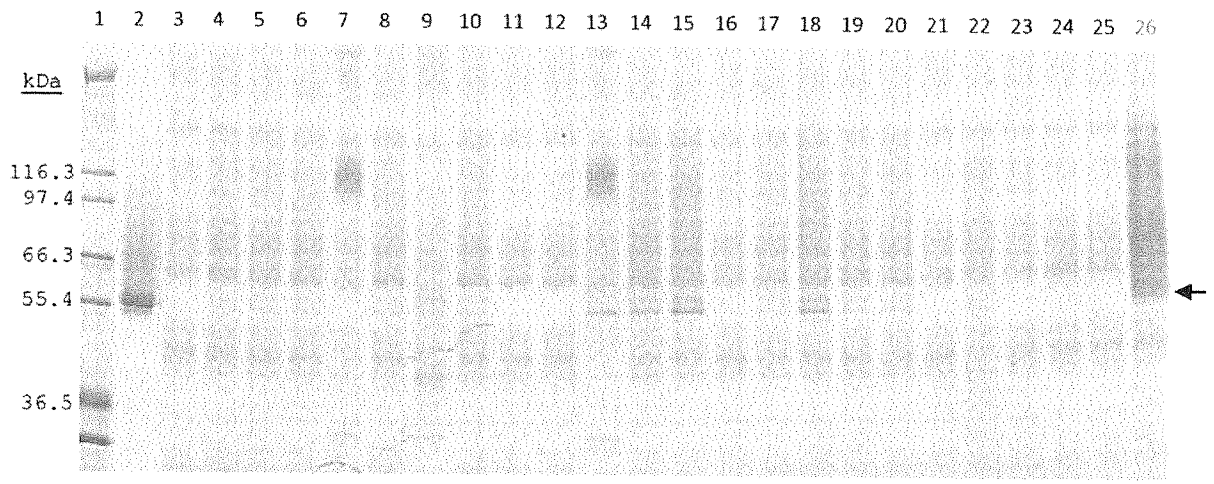
FIG. 5. Coomassie stain of culture supernatant isolated from clones with LP1 (pFJP6014, ruLAPII_short) strain background. 7.5 μL of culture supernatant were loaded onto a 12% Bis-Tris SDS gel, 26-Well, MES buffer under reducing conditions. A) SDS PAGE/Coomassie stain, Black arrow indicates the position of the ruLAPII product; B) Loading scheme, Black: clones chosen for later high cell density fermentation, Green: reference strain.

In contrast to clones producing ruDPPIV, no or very low product amount was visible in the culture supernatant of clones producing ruLAPII (FIG. 5A) which could be explained due to the strong glycosylation of ruLAPII (i.e. no sharp band but rather fuzzy band) making it difficult to quantify. Despite this difficulties to identify high producers, several clones showed promising results: LP1 (pFJP6014.6) (FIG. 5, lane 13), LP1 (pFJP6014.12) (FIG. 5, lane 14), LP1 (pFJP6014.13) (FIG. 5, lane 15), LP1 (pFJP6014.20) (FIG. 5, lane 18) and LP1 (pFJP6014.15) (FIG. 5, lane 19). Overall, the product amount secreted by ruLAPII_short clones was significantly lower compared to reference strain LP1 (pCKP6011.4).

The culture supernatant of all clones was analyzed for enzymatic activity using the AMC assay (See Example 1, section 7.6). As expected, the culture supernatant of clones showing the highest product titer also showed the highest enzymatic activity. The highest activity was found in the culture supernatant of clone LP1 (pFJP6014.13) (26.1 U/L) which was approximately 15% of the activity measured in the reference strain LP1 (pCKP6011.4) (173.8 U/L). The reference clone showed a similar activity as in the initial screening (158.4 U/L; ResRep 2014.111). In summary, the data suggested that the short variant are still enzymatically active.

Example 3: Secondary Screening

The expression with the AOX1 promoter is induced by a limited methanol feed. The batch phase of about 24-28 hours (indicated by a pO2 spike) is followed by a glycerol fed batch phase to increase biomass. After 12 hrs of glycerol feed, the methanol feed is started, depending on the fermentation protocol for either ruDPPIV or ruLAPII. Aside the five clones of either the short variant of ruDPPIV or ruLAPII, the reference strains were included for direct comparison.

TABLE 2

Parameter Setup for Ambr250 fermentation

| Strain | Product | Enzymatic activity in primary screening [U/L] |
|---|---|---|
| LP1 (pFJP6015.8) | ruDPPIV_short | 2032 |
| LP1 (pFJP6015.6) | ruDPPIV_short | 1898 |
| LP1 (pFJP6015.18) | ruDPPIV_short | 1614 |
| LP1 (pFJP6015.12) | ruDPPIV_short | 1394 |
| LP1 (pFJP6015.15) | ruDPPIV_short | 1353 |
| LP1 (pCKP6003.1) | ruDPPIV | 4325 |
| LP1 (pFJP6014.13) | ruLAPII_short | 26.1 |
| LP1 (pFJP6014.20) | ruLAPII_short | 19.3 |
| LP1 (pFJP6014.6) | ruLAPII_short | 11.6 |
| LP1 (pFJP6014.12) | ruLAPII_short | 14.1 |
| LP1 (pFJP6014.15) | ruLAPII_short | 7.1 |
| LP1 (pCKP6011.4) | ruLAPII | 173.8 |

1. ruDPPIV_short 1.1 Biomass Generation

The cell density and the dry cell weight of all fermentation runs were compared to each other. The duration of the batch phase for all fermentations was predetermined by the initial glycerol concentration of 45 g $L^{-1}$ glycerol and the starting OD600 of 1 for all strains and the batch phase ended (indicated by a pO2 spike) between 18 and 20 hours. Subsequently, a glycerol feed started for 12 hours, followed by a methanol feed. The whole fermentation duration was 78 hours.

Figure 6:
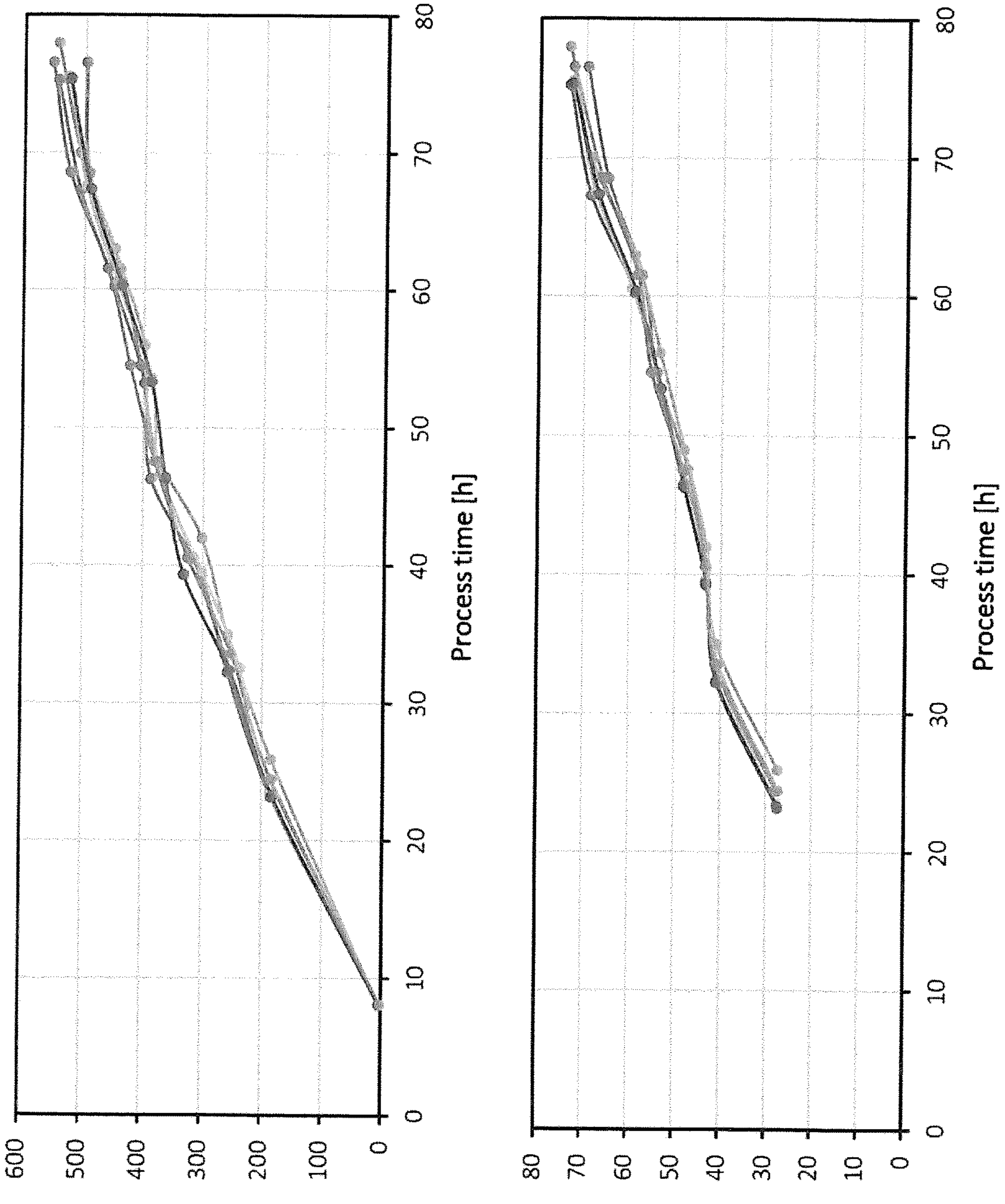
FIG. 6. Biomass generation of clones with LP1 (pFJP6015, ruDPPIV_short) strain background. LP1 (pFJP6015.8), LP1 (pFJP6015.6), LP1 (pFJP6015.18), LP1 (pFJP6015.12), LP1 (pFJP6015.15), LP1 (pCKP6003.1). A) Optical density OD600; B) Dry cell weight DCW.

No significant differences in biomass (less than 10% deviation from median WCW and less than 1% deviation from median DCW) were observed at the end of fermentation. This indicated that the strains were not affected by the short variants of ruDPPIV. Slight differences were observed in optical density but were most likely analytical errors due to the high cell density of the culture (FIG. 6).

1.2 Product Generation

Several samples were taken along the fermentation runs to investigate ruDPPIV_short product increase and to identify the most promising strains, respectively. The cells were centrifuged and the culture supernatant isolated. Subsequently, representative samples were analyzed via SDS PAGE/Coomassie stain.

Figure 7:
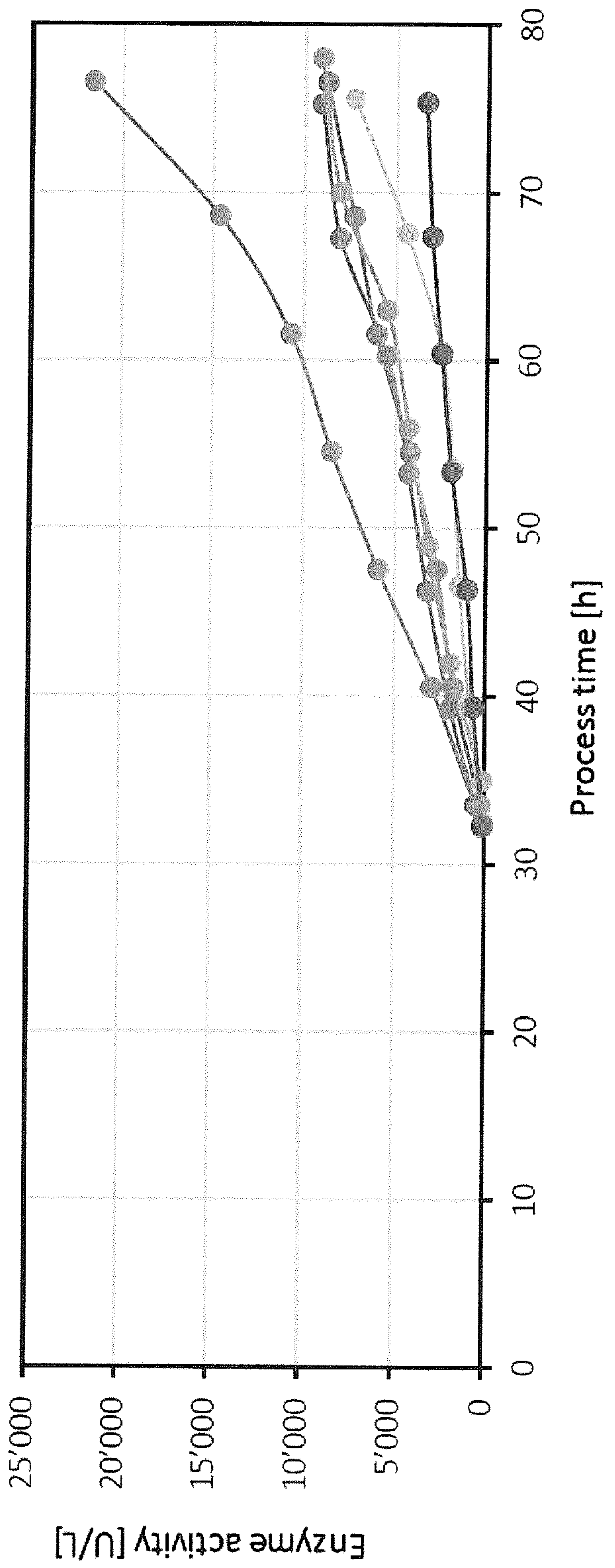
FIG. 7. Enzymatic activity of clones with LP1 (pFJP6015, ruDPPIV_short) strain background. LP1 (pFJP6015.8), LP1 (pFJP6015.6), LP1 (pFJP6015.18), LP1 (pFJP6015.12), LP1 (pFJP6015.15), LP1 (pCKP6003.1). Activity measurement (AMC assay) was done according to SOP provided by AMYRA.

As expected from data of the primary screening, the product titer of ruDPPIV_short was significantly decreased compared to the full-length product ruDPPIV (FIG. 7, compare green line with other lines). No significant difference was observed in activity when the culture supernatants of the best producing ruDPPIV_short clones [without clone LP1 (pFJP6015.15)] were compared with each other; i.e. enzymatic activity ranged between 7'276.6 U/L and 9'055.6 U/L). Compared to wildtype strain LP1 (pCKP6003.1), the activity of the best producing ruDPPIV_short clone was approximately 50% of the reference strain LP1 (pCKP6003.1) (21'586 U/L) (FIG. 7). The activity of the reference clone LP1 (pCKP6003.1) was in line with previous data (25'000 U/L; 10 L Infors, report 2014.157).

2. ruLAPII_short 2.1 Biomass Generation

The cell density and the dry cell weight of all fermentation runs were compared to each other. The duration of the batch phase for all fermentations was predetermined by the initial glycerol concentration of 45 g $L^{-1}$ glycerol and the starting OD600 of 1 for all strains and the batch phase ended (indicated by a pO2 spike) between 18 and 20 hours. Subsequently, a glycerol feed started for 12 hours, followed by a methanol feed. The whole fermentation duration was 78 hours.

Figure 8:
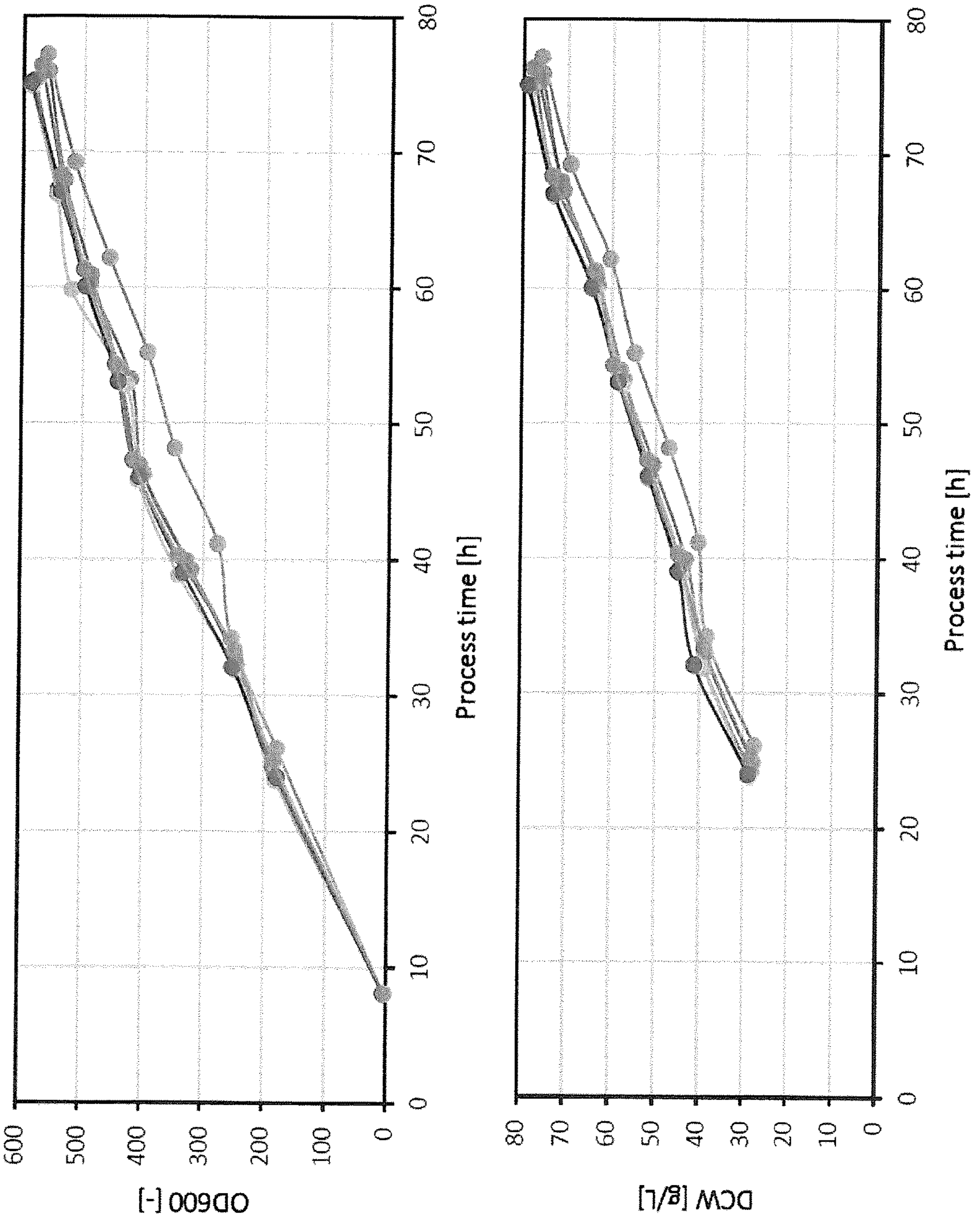
FIG. 8. Biomass generation of clones with LP1 (pFJP6014, ruLAPII_short) strain background. LP1 (pFJP6014.13), LP1 (pFJP6014.20), LP1 (pFJP6014.6), LP1 (pFJP6014.12), LP1 (pFJP6014.15), LP1 (pCKP6011.4). A) Optical density OD600; B) Dry cell weight DCW.

No significant differences in biomass (less than 10% deviation from median WCW and less than 1% deviation from median DCW) were observed at the end of fermentation, indicating that the clones producing the short variants grow similar to the clones producing full length ruLAPII. Slight differences were observed in optical density but were most likely analytical errors due to the high cell density of the culture medium (FIG. 8).

2.2 Product Generation

Several samples were taken along the fermentation runs to investigate ruLAPII_short product increase and to identify the most promising strains, respectively. The cells were centrifuged and the culture supernatant was isolated. Subsequently, representative samples were analyzed via SDS PAGE/Coomassie stain and AMC assay.

Figure 9:
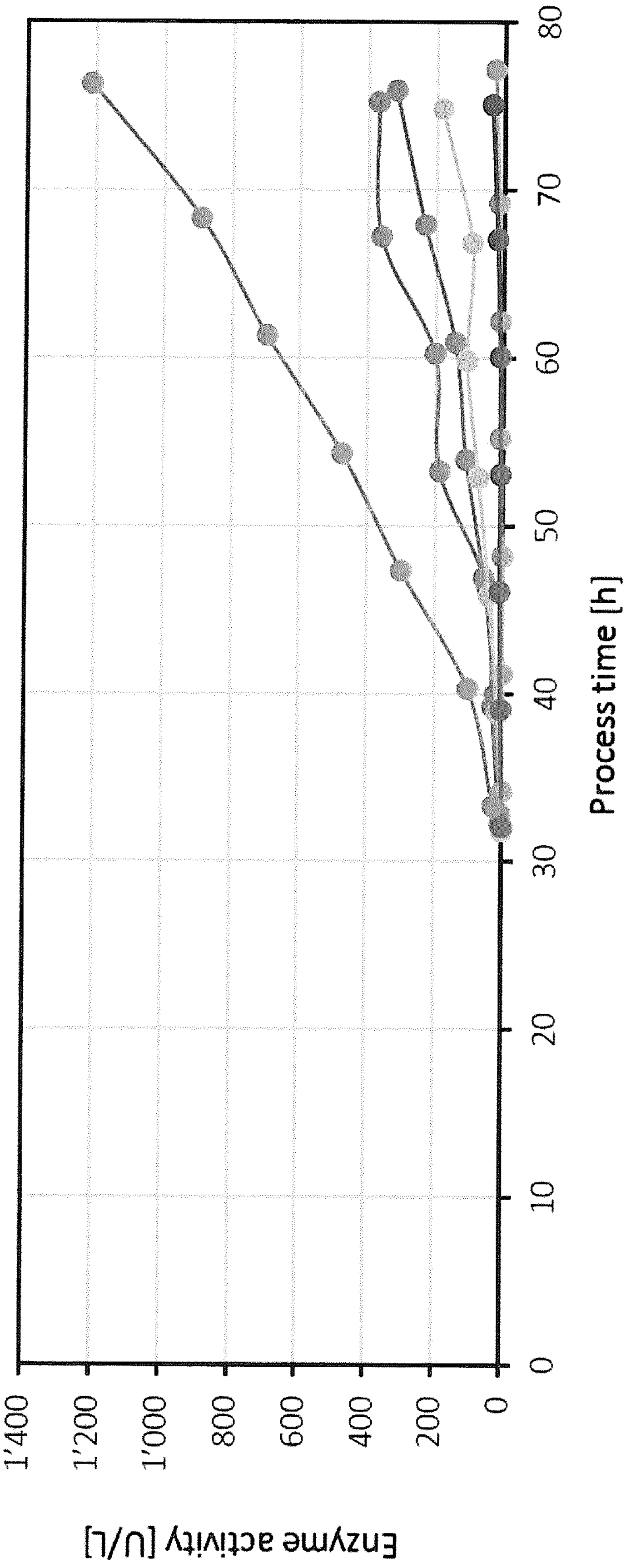
FIG. 9. Enzymatic activity of clones with LP1 (pFJP6014, ruLAPII_short) strain background. LP1 (pFJP6014.13), LP1 (pFJP6014.20), LP1 (pFJP6014.6), LP1 (pFJP6014.12), LP1 (pFJP6014.15), LP1 (pCKP6011.4). Activity measurement (AMC assay) was done according to SOP provided by AMYRA.

Similar to ruDPPIV_short and as expected from data of the primary screening, product titer of ruLAPII_short was significantly decreased compared to the full length ruLAPII (FIG. 9, compare green line with other lines). The strain ranking was identical as observed in the primary screening. No strong differences were observed in activity when the culture supernatant of the best two producing ruLAPII_short clones were compared to each other; i.e. enzymatic activity ranged between 320 U/L and 371.2 U/L). Compared to wild type strain LP1 (pCKP6011.4), the activity of the best producing ruLAPII_short clone was approximately 30% of the reference strain LP1 (pCKP6011.4) (1'212.3 U/L) (FIG. 9). The activity of the reference clone LP1 (pCKP6011.4) was in line with previous data (1'500 U/L; 10 L Infors, report 2014.157).

Example 4: Specific Activity

As shown in Examples 2 and 3, the volumetric activity (U/L) of the short variants of ruDPPIV or ruLAPII were significantly reduced. As the product amount was also significantly reduced, it was not clear whether the reduced activity was due to lower specific activity or due to lower product amount in the culture supernatant. Thus, to assess the specific activity, it was decided to purify the proteins and assess the specific activity (i.e. U/mg). For that purpose, the purification strategy from "GLH-003: DPP4 and LAP2 step elution feasibility" (Presentation; A. Zurbriggen et al., 2016) was adapted for use in batch mode.

1. ruDPPIV_short 12 mL of the culture supernatant from LP1 (pFJP6015.6; ruDPPI_short; 9'056 U/L) and LP1 (pCKP6003.1; ruDPPIV; 21'586 U/L) were loaded onto 2 mL SP Sepharose XL (GE Healthcare) and subsequently eluted in 2 mL 25 mM Tris, pH 7.2, 130 mM NaCl after 2× washing with 10 mL 25 mM Tris, pH 7.2, 20 mM NaCl. From purification samples (Load, flow through and elution), AMC assay (activity assay) and BCA assay (protein concentration) was done. Three trials were done: in the first purification trial, a technical issue occurred and thus data could not be trusted. In a third trial, the aim was to generate more purified material for subsequent mass spectroscopy. Despite increasing sample volume and resin, binding capacity was already reached and no improvement in material supply could be generated. For convenience, data of the second purification trial will be presented.

Figure 10:
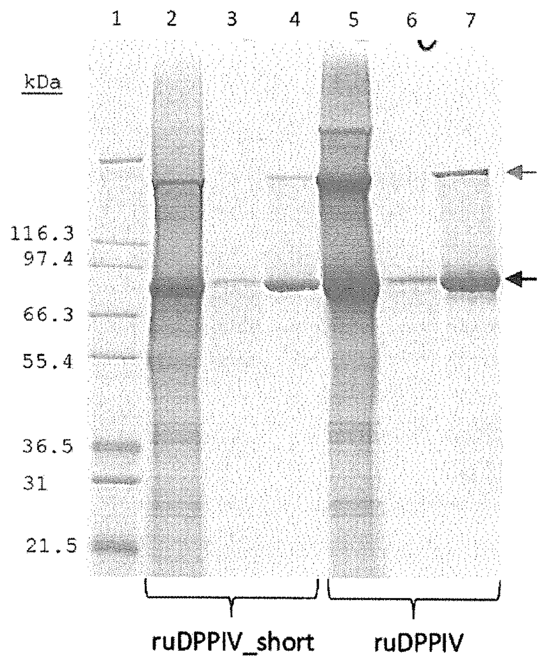
FIG. 10. Coomassie stain of purification isolated from clones with LP1 (pFJP6015, ruDPPIV_short) strain background. 7.5 μL of culture supernatant were loaded onto a 12% Bis-Tris SDS gel, 26-Well, MES buffer under reducing conditions. A) SDS PAGE/Coomassie stain, Black arrow indicates the position of the ruDPPIV product, Blue arrow indicates the position of a higher molecular weight variant of ruDPPIV.; B) Loading scheme.

After purification, samples were loaded onto an SDS-PAGE/Coomassie stain and BCA assay together with AMC assay was done (FIG. 10).

No strong differences were found in the specific activity (12 U/mg) between ruDPPIV_short and ruDPPIV. For comparison, ruDPPIV purified material of the tox material generation (Report ResRep2014.165) showed a specific activity of 19.6 U/mg and 20 U/mg; Demonstration runs showed an activity of 18.3 U/mg and 17.9 U/mg. The differences of ruDPPIV between the data presented here and the material generation report is most likely attributed to the different resin mode (batch mode vs column mode).

2. ruLAPII_short 12 mL of the culture supernatant from LP1 (pFJP6014.13; ruLAPII_short; 371 U/L) and LP1 (pCKP6011.4; ruLAPII; 1'212 U/L) were loaded onto 2 mL SP Sepharose XL (GE Healthcare) and subsequently eluted in 2 mL 20 mM Na-Phosphate, pH 6.0, 130 mM NaCl after 2× washing with 10 mL 20 mM Na-Phosphate, pH 6.0. From purification samples (Load, flow through and elution), AMC assay (activity assay) and BCA assay (protein concentration) was done. Three trials were done: in the first purification trial, a technical issue occurred and thus data could not be trusted. In a third trial, the aim was to generate more purified material for subsequent mass spectroscopy. Similar to the ruDPPIV_short purification binding capacity was already reached and no improvement in material supply could be generated. For convenience, data of the second purification trial will be presented.

Figure 11:
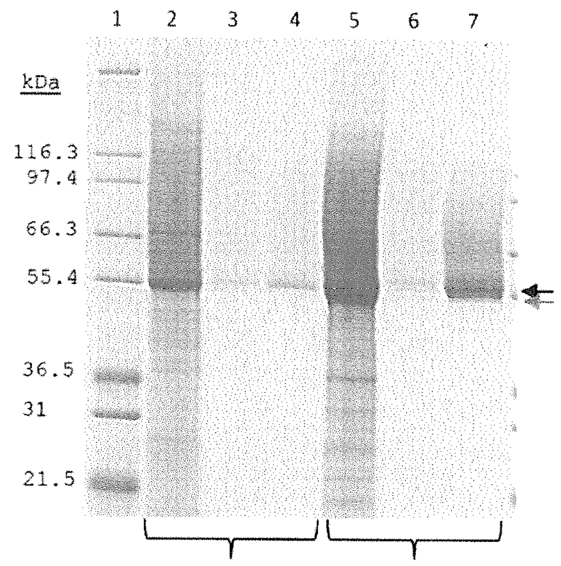
FIG. 11. Coomassie stain of purification isolated from clones with LP1 (pFJP6014.13, ruLAPII_short) strain background. 7.5 μL of culture supernatant were loaded onto a 12% Bis-Tris SDS gel, 26-Well, MES buffer under reducing conditions. A) SDS PAGE/Coomassie stain, Black arrow indicates the position of the ruLAPII product, Blue arrow indicates the position of a molecular weight variant of ruLAPII; B) Loading scheme.

After purification, samples were loaded onto an SDS-PAGE/Coomassie stain and BCA assay together with AMC assay was done (FIG. 11).

Slightly lower specific activity was found in purified samples of ruLAPII_short which was approximately 26% lower (i.e. 1.1 U/mg versus 1.5 U/mg) than with full length ruLAPII. When the samples were compared on a Coomassie stained SDS gel, less variant was found at the expected position (FIG. 11, compare lane 3&6 or lane 4&7; blue arrow). Specific activity of ruLAPII (1.5 U/mg) was slightly lower than observed during tox material generation (1.7 U/mg and, Report ResRep2014.165) and Demo Run (1.9 U/mg and 2 U/mg). Similar to ruDPPIV purification, the difference could be explained by the use of a slightly different purification strategy (i.e. batch mode vs column mode).

Example 4: Product Degradation

Aim of this study was to confirm that the short variant of ruDPPIV and ruLAPII do not further degrade as observed with the full-length molecule. For this purpose, mass spectroscopy (ESI-MS and Maldi-TOF) was done. Briefly, after purification, the elution samples were further processed with PNGase F to cleave off glycan structures (which would disturb Mass spectroscopy) and Amicon desalting to remove free glycans.

1. ruDPPIV_short

First, ESI-MS and Maldi-TOF was done by B-Fabric. For ESI-MS, the signal intensities were very low, or no protein-like species could be detected at all. Traces of PNGaseF (34'874 Da and 34'887 Da) were detected.

Figure 12:
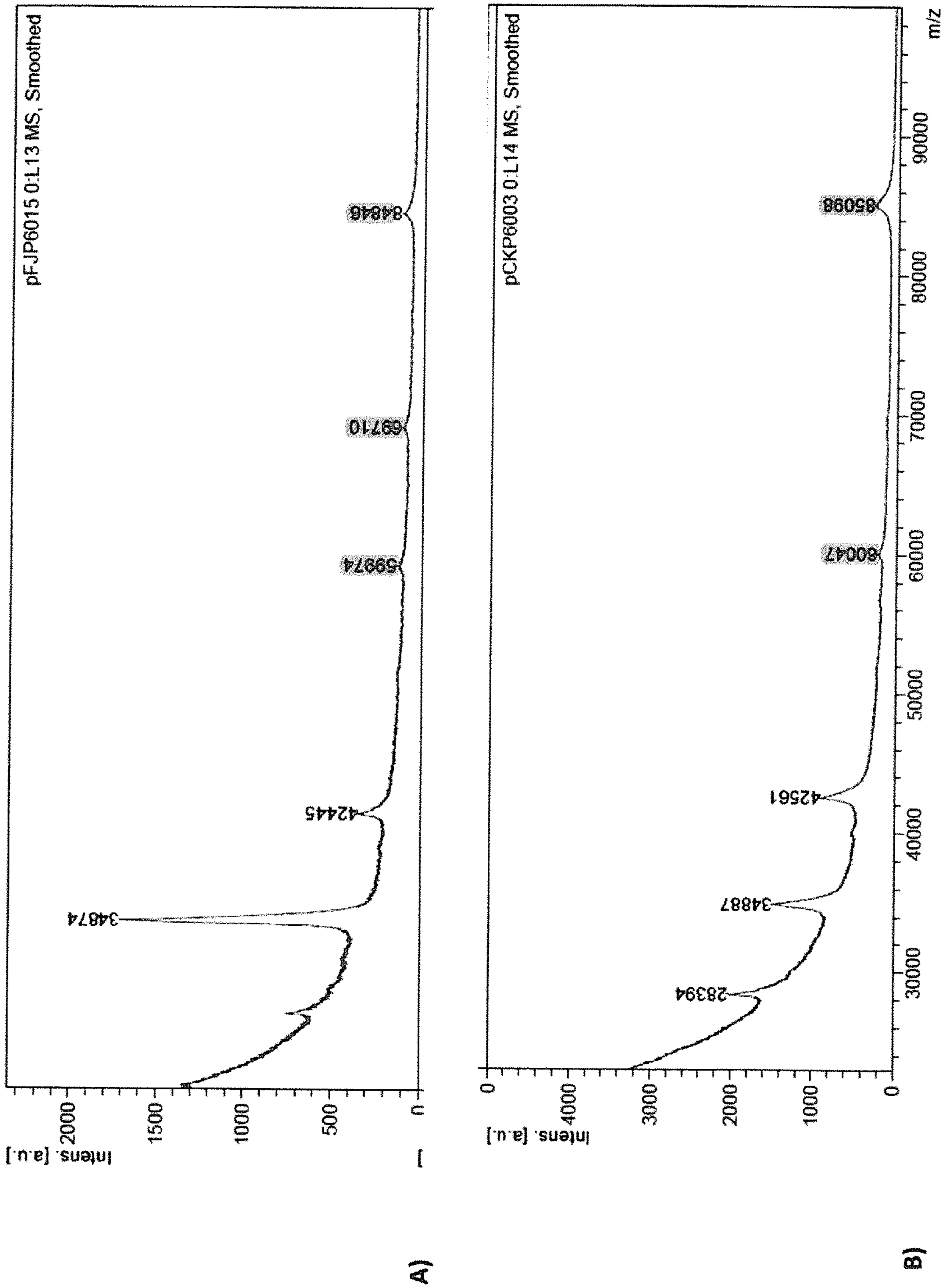
FIG. 12. Mass spectroscopy (Maldi-TOF) of ruDPPIV. 40 μl of PNGase digested elution samples were analyzed via Maldi-TOF (see Example 1, section 7.10). A) ruDPPIV-_short; expected mass: 84'802; B) ruDPPIV; expected mass: 86'486.

For both variants, degradation was observed in Maldi-TOF. In contrast to full-length ruDPPIV, full length ruDPPIV_short molecule could be found with most likely acetylation modification (+42) (FIG. 12).

2. ruLAPII_short

Figure 13:
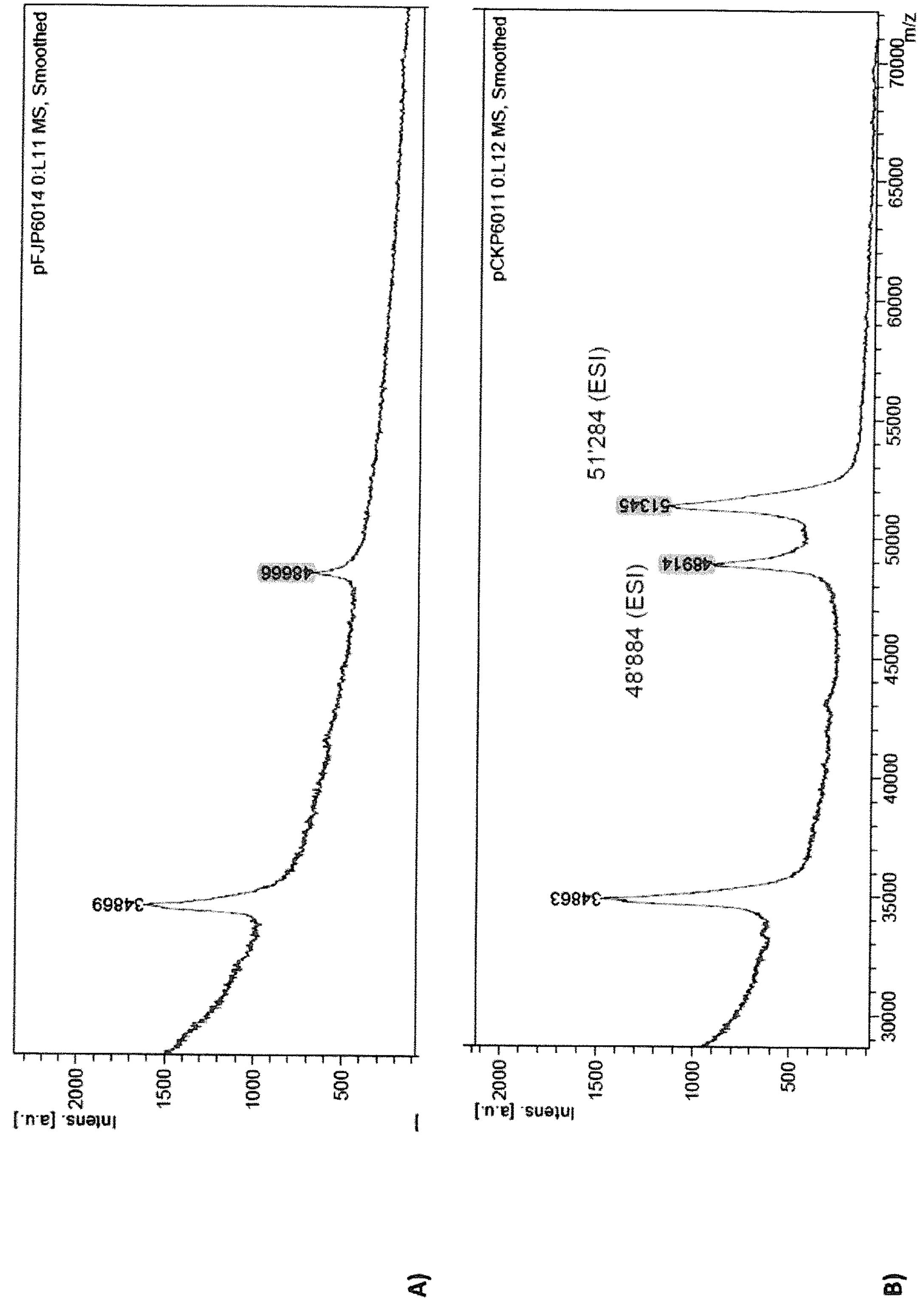
FIG. 13. Mass spectroscopy of ruLAPII. 40 μL of PNGase digested elution samples were analyzed via Maldi-TOF (see Example 1, section 7.10). A) ruLAPII_short; expected mass: 48'696; B) ruLAPII; expected mass: 51'714. Numbers in red indicate ESI data.

First, ESI-MS and Maldi-TOF was done by B-Fabric. For ESI-MS, only samples of the full-length molecule ruLAPII was found. Traces of PNGaseF (34'869 Da and 34'863 Da) were detected. With Maldi-TOF, only full-length molecule was detected for ruLAPII short. For the full-length ruLAPII, molecule, only degradation could be identified. For full-length ruLAPII, the main cleavage occurred after Val4 and Lys457 (48'884 da) and only after Val4 (51'284 da) with was in line with previous data supplied by Biomeva (FIG. 13).

Abbreviations

| Abbreviation | Explanation |
|---|---|
| AA | Amino acid |
| AMC | 7-Amino-4-methylcoumarin; substrate for leucine and dipeptidyl aminopeptidase |
| CDW | Cell dry weight |
| CFM | Cell free medium |
| Da | Unified atomic mass unit |
| EoF | End of Fermentation samples |
| Hrs | Hours |
| IPC | In-process controls |
| kDa | Kilo Dalton |
| LabChip GX II | Instrument (PerkinElmer), microfluidic gel electrophoresis |
| MeOH | Methanol |
| MQ | Milli-Q water; made by passing the source water through mixed bed ion exchange and organics (activated charcoal) cartridges |
| OD600 | Optical density/absorbance at 600 nm |
| PBS | Phosphate buffered saline |
| PAOX1 | Promoter AOX1, induced by methanol |
| pI | Isoelectric point |
| ruDPPIV | Dipeptidyl-peptidase IV from *Trichophyton rubrum* |
| ruLAPII | Leucine aminopeptidases II from *Trichophyton rubrum* |
| rpm | Revolutions per minute |
| SDS PAGE | Analytical method; Sodium dodecyl sulfate polyacrylamide gel electrophoresis |
| YPC | Growth medium; yeast extract, peptone, citrate buffer, pH 6.0 |
| WCW | Wet cell weight |

The invention claimed is:

1. A polypeptide comprising a truncated dipeptidylpeptidase IV (DPPIV) polypeptide, wherein:

(i) 12 to 15 amino acids are missing at the C-terminus compared to the wildtype DPPIV polypeptide; or (ii) 12 to 15 amino acids are missing at the C-terminus compared to the wildtype DPPIV polypeptide and one or two amino acids are missing at the N-terminus, and wherein the wildtype DPPIV polypeptide consists of the amino acid sequence set forth in SEQ ID NO: 1.

2. The DPPIV polypeptide of claim 1, wherein 12 to 14 amino acids are missing at the C-terminus compared to the wildtype DPPIV polypeptide.

3. The DPPIV polypeptide of claim 1, wherein 13 or 14 amino acids are missing at the C-terminus compared to the wildtype DPPIV polypeptide.

4. A polypeptide selected from the group consisting of:

(i) a polypeptide comprising a truncated DPPIV polypeptide consisting of residues 1-748 of the amino acid sequence set forth in SEQ ID NO: 1;

(ii) a polypeptide comprising a truncated DPPIV polypeptide consisting of residues 1-747 of the amino acid sequence set forth in SEQ ID NO: 1;

(iii) a polypeptide comprising a truncated DPPIV polypeptide consisting of residues 1-746 of the amino acid sequence set forth in SEQ ID NO: 1;

(iv) a polypeptide comprising a truncated DPPIV polypeptide consisting of residues 1-745 of the amino acid sequence set forth in SEQ ID NO: 1;

(v) a polypeptide comprising a truncated DPPIV polypeptide consisting of residues 2-748 of the amino acid sequence set forth in SEQ ID NO: 1;

(vi) a polypeptide comprising a truncated DPPIV polypeptide consisting of residues 2-747 of the amino acid sequence set forth in SEQ ID NO: 1

(vii) a polypeptide comprising a truncated DPPIV polypeptide consisting of residues 2-746 of the amino acid sequence set forth in SEQ ID NO: 1; and (viii) a polypeptide comprising a truncated DPPIV polypeptide consisting of residues 2-745 of the amino acid sequence set forth in SEQ ID NO: 1.

5. The polypeptide of claim 1, which is derived from *Trichophyton rubrum*.

6. The polypeptide of claim 1, which cleaves the dipeptide motive NH2-X-Pro off the N-terminal end of polypeptides.

7. The polypeptide of claim 1, which is produced in *Pichia pastoris*.

8. A composition comprising the polypeptide according to claim 1 and a pharmaceutically acceptable carrier.

9. A composition comprising the polypeptide according to claim 4 and a pharmaceutically acceptable carrier.

* * * * *

SEQUENCE LISTING

```
<160> NUMBER OF SEQ ID NOS: 25

<210> SEQ ID NO 1
<211> LENGTH: 760
<212> TYPE: PRT
<213> ORGANISM: Artificial Sequence
<220> FEATURE:
<223> OTHER INFORMATION: Dipeptidylpeptidase

<400> SEQUENCE: 1

Ile Val Pro Pro Arg Glu Pro Arg Ser Pro Thr Gly Gly Gly Asn Lys
1               5                   10                  15

Leu Leu Thr Tyr Lys Glu Cys Val Pro Arg Ala Thr Ile Ser Pro Arg
            20                  25                  30

Ser Thr Ser Leu Ala Trp Ile Asn Ser Glu Glu Asp Gly Arg Tyr Ile
        35                  40                  45

Ser Gln Ser Asp Asp Gly Ala Leu Ile Leu Gln Asn Ile Val Thr Asn
    50                  55                  60

Thr Asn Lys Thr Leu Val Ala Ala Asp Lys Val Pro Lys Gly Tyr Tyr
65                  70                  75                  80

Asp Tyr Trp Phe Lys Pro Asp Leu Ser Ala Val Leu Trp Ala Thr Asn
```

-continued

```
                85                  90                  95

Tyr Thr Lys Gln Tyr Arg His Ser Tyr Phe Ala Asn Tyr Phe Ile Leu
            100                 105                 110

Asp Ile Lys Lys Gly Ser Leu Thr Pro Leu Ala Gln Asp Gln Ala Gly
        115                 120                 125

Asp Ile Gln Tyr Ala Gln Trp Ser Pro Met Asn Asn Ser Ile Ala Tyr
    130                 135                 140

Val Arg Gly Asn Asp Leu Tyr Ile Trp Asn Asn Gly Lys Thr Lys Arg
145                 150                 155                 160

Ile Thr Glu Asn Gly Gly Pro Asp Ile Phe Asn Gly Val Pro Asp Trp
                165                 170                 175

Val Tyr Glu Glu Glu Ile Phe Gly Asp Arg Phe Ala Leu Trp Phe Ser
            180                 185                 190

Pro Asp Gly Glu Tyr Leu Ala Tyr Leu Arg Phe Asn Glu Thr Gly Val
        195                 200                 205

Pro Thr Tyr Thr Ile Pro Tyr Tyr Lys Asn Lys Gln Lys Ile Ala Pro
    210                 215                 220

Ala Tyr Pro Arg Glu Leu Glu Ile Arg Tyr Pro Lys Val Ser Ala Lys
225                 230                 235                 240

Asn Pro Thr Val Gln Phe His Leu Leu Asn Ile Ala Ser Ser Gln Glu
                245                 250                 255

Thr Thr Ile Pro Val Thr Ala Phe Pro Glu Asn Asp Leu Val Ile Gly
            260                 265                 270

Glu Val Ala Trp Leu Ser Ser Gly His Asp Ser Val Ala Tyr Arg Ala
        275                 280                 285

Phe Asn Arg Val Gln Asp Arg Glu Lys Ile Val Ser Val Lys Val Glu
    290                 295                 300

Ser Lys Glu Ser Lys Val Ile Arg Glu Arg Asp Gly Thr Asp Gly Trp
305                 310                 315                 320

Ile Asp Asn Leu Leu Ser Met Ser Tyr Ile Gly Asn Val Asn Gly Lys
                325                 330                 335

Glu Tyr Tyr Val Asp Ile Ser Asp Ala Ser Gly Trp Ala His Ile Tyr
            340                 345                 350

Leu Tyr Pro Val Asp Gly Gly Lys Glu Ile Ala Leu Thr Lys Gly Glu
        355                 360                 365

Trp Glu Val Val Ala Ile Leu Lys Val Asp Thr Lys Lys Lys Leu Ile
    370                 375                 380

Tyr Phe Thr Ser Thr Lys Tyr His Ser Thr Thr Arg His Val Tyr Ser
385                 390                 395                 400

Val Ser Tyr Asp Thr Lys Val Met Thr Pro Leu Val Asn Asp Lys Glu
                405                 410                 415

Ala Ala Tyr Tyr Thr Ala Ser Phe Ser Ala Lys Gly Gly Tyr Tyr Ile
            420                 425                 430

Leu Ser Tyr Gln Gly Pro Asn Val Pro Tyr Gln Glu Leu Tyr Ser Thr
        435                 440                 445

Lys Asp Ser Lys Lys Pro Leu Lys Thr Ile Thr Ser Asn Asp Ala Leu
    450                 455                 460

Leu Glu Lys Leu Lys Glu Tyr Lys Leu Pro Lys Val Ser Phe Phe Glu
465                 470                 475                 480

Ile Lys Leu Pro Ser Gly Glu Thr Leu Asn Val Lys Gln Arg Leu Pro
                485                 490                 495

Pro Asn Phe Asn Pro His Lys Lys Tyr Pro Val Leu Phe Thr Pro Tyr
            500                 505                 510
```

```
Gly Gly Pro Gly Ala Gln Glu Val Ser Gln Ala Trp Asn Ser Leu Asp
        515                 520                 525

Phe Lys Ser Tyr Ile Thr Ser Asp Pro Glu Leu Glu Tyr Val Thr Trp
    530                 535                 540

Thr Val Asp Asn Arg Gly Thr Gly Tyr Lys Gly Arg Lys Phe Arg Ser
545                 550                 555                 560

Ala Val Ala Lys Arg Leu Gly Phe Leu Glu Ala Gln Asp Gln Val Phe
                565                 570                 575

Ala Ala Lys Glu Val Leu Lys Asn Arg Trp Ala Asp Lys Asp His Ile
            580                 585                 590

Gly Ile Trp Gly Trp Ser Tyr Gly Gly Phe Leu Thr Ala Lys Thr Leu
        595                 600                 605

Glu Thr Asp Ser Gly Val Phe Thr Phe Gly Ile Ser Thr Ala Pro Val
    610                 615                 620

Ser Asp Phe Arg Leu Tyr Asp Ser Met Tyr Thr Glu Arg Tyr Met Lys
625                 630                 635                 640

Thr Val Glu Leu Asn Ala Asp Gly Tyr Ser Glu Thr Ala Val His Lys
                645                 650                 655

Val Asp Gly Phe Lys Asn Leu Lys Gly His Tyr Leu Ile Gln His Gly
            660                 665                 670

Thr Gly Asp Asp Asn Val His Phe Gln Asn Ala Ala Val Leu Ser Asn
        675                 680                 685

Thr Leu Met Asn Gly Gly Val Thr Ala Asp Lys Leu Thr Thr Gln Trp
    690                 695                 700

Phe Thr Asp Ser Asp His Gly Ile Arg Tyr Asp Met Asp Ser Thr Tyr
705                 710                 715                 720

Gln Tyr Lys Gln Leu Ser Lys Met Val Tyr Asp Gln Lys Gln Arg Arg
                725                 730                 735

Pro Glu Ser Pro Pro Met His Gln Trp Ser Lys Arg Val Leu Ala Ala
            740                 745                 750

Leu Phe Gly Glu Arg Ala Glu Glu
        755                 760


<210> SEQ ID NO 2
<211> LENGTH: 479
<212> TYPE: PRT
<213> ORGANISM: Artificial Sequence
<220> FEATURE:
<223> OTHER INFORMATION: Leucine aminopeptidase

<400> SEQUENCE: 2

His Pro Val Val Gly Gln Glu Pro Phe Gly Trp Pro Phe Lys Pro Met
1               5                   10                  15

Val Thr Gln Asp Asp Leu Gln Asn Lys Ile Lys Leu Lys Asp Ile Met
            20                  25                  30

Ala Gly Val Glu Lys Leu Gln Ser Phe Ser Asp Ala His Pro Glu Lys
        35                  40                  45

Asn Arg Val Phe Gly Gly Asn Gly His Lys Asp Thr Val Glu Trp Ile
    50                  55                  60

Tyr Asn Glu Ile Lys Ala Thr Gly Tyr Tyr Asp Val Lys Lys Gln Glu
65                  70                  75                  80

Gln Val His Leu Trp Ser His Ala Glu Ala Ala Leu Asn Ala Asn Gly
                85                  90                  95

Lys Asp Leu Lys Ala Ser Ala Met Ser Tyr Ser Pro Pro Ala Ser Lys
            100                 105                 110
```

-continued

```
Ile Met Ala Glu Leu Val Val Ala Lys Asn Asn Gly Cys Asn Ala Thr
        115                 120                 125

Asp Tyr Pro Ala Asn Thr Gln Gly Lys Ile Val Leu Val Glu Arg Gly
    130                 135                 140

Val Cys Ser Phe Gly Glu Lys Ser Ala Gln Ala Gly Asp Ala Lys Ala
145                 150                 155                 160

Ala Gly Ala Ile Val Tyr Asn Asn Val Pro Gly Ser Leu Ala Gly Thr
                165                 170                 175

Leu Gly Gly Leu Asp Lys Arg His Val Pro Thr Ala Gly Leu Ser Gln
            180                 185                 190

Glu Asp Gly Lys Asn Leu Ala Thr Leu Val Ala Ser Gly Lys Ile Asp
        195                 200                 205

Val Thr Met Asn Val Ile Ser Leu Phe Glu Asn Arg Thr Thr Trp Asn
    210                 215                 220

Val Ile Ala Glu Thr Lys Gly Gly Asp His Asn Asn Val Ile Met Leu
225                 230                 235                 240

Gly Ala His Ser Asp Ser Val Asp Ala Gly Pro Gly Ile Asn Asp Asn
                245                 250                 255

Gly Ser Gly Ser Ile Gly Ile Met Thr Val Ala Lys Ala Leu Thr Asn
            260                 265                 270

Phe Lys Leu Asn Asn Ala Val Arg Phe Ala Trp Trp Thr Ala Glu Glu
        275                 280                 285

Phe Gly Leu Leu Gly Ser Thr Phe Tyr Val Asn Ser Leu Asp Asp Arg
    290                 295                 300

Glu Leu His Lys Val Lys Leu Tyr Leu Asn Phe Asp Met Ile Gly Ser
305                 310                 315                 320

Pro Asn Phe Ala Asn Gln Ile Tyr Asp Gly Asp Gly Ser Ala Tyr Asn
                325                 330                 335

Met Thr Gly Pro Ala Gly Ser Ala Glu Ile Glu Tyr Leu Phe Glu Lys
            340                 345                 350

Phe Phe Asp Asp Gln Gly Ile Pro His Gln Pro Thr Ala Phe Thr Gly
        355                 360                 365

Arg Ser Asp Tyr Ser Ala Phe Ile Lys Arg Asn Val Pro Ala Gly Gly
    370                 375                 380

Leu Phe Thr Gly Ala Glu Val Val Lys Thr Pro Glu Gln Val Lys Leu
385                 390                 395                 400

Phe Gly Gly Glu Ala Gly Val Ala Tyr Asp Lys Asn Tyr His Arg Lys
                405                 410                 415

Gly Asp Thr Val Ala Asn Ile Asn Lys Gly Ala Ile Phe Leu Asn Thr
            420                 425                 430

Arg Ala Ile Ala Tyr Ala Ile Ala Glu Tyr Ala Arg Ser Leu Lys Gly
        435                 440                 445

Phe Pro Thr Arg Pro Lys Thr Gly Lys Arg Asp Val Asn Pro Gln Tyr
    450                 455                 460

Ser Lys Met Pro Gly Gly Gly Cys Gly His His Thr Val Phe Met
465                 470                 475
```

<210> SEQ ID NO 3
<211> LENGTH: 745
<212> TYPE: PRT
<213> ORGANISM: Artificial Sequence
<220> FEATURE:
<223> OTHER INFORMATION: Dipeptidylpeptidase

<400> SEQUENCE: 3

-continued

```
Val Pro Pro Arg Glu Pro Arg Ser Pro Thr Gly Gly Gly Asn Lys Leu
1               5                   10                  15

Leu Thr Tyr Lys Glu Cys Val Pro Arg Ala Thr Ile Ser Pro Arg Ser
            20                  25                  30

Thr Ser Leu Ala Trp Ile Asn Ser Glu Glu Asp Gly Arg Tyr Ile Ser
        35                  40                  45

Gln Ser Asp Asp Gly Ala Leu Ile Leu Gln Asn Ile Val Thr Asn Thr
    50                  55                  60

Asn Lys Thr Leu Val Ala Ala Asp Lys Val Pro Lys Gly Tyr Tyr Asp
65                  70                  75                  80

Tyr Trp Phe Lys Pro Asp Leu Ser Ala Val Leu Trp Ala Thr Asn Tyr
                85                  90                  95

Thr Lys Gln Tyr Arg His Ser Tyr Phe Ala Asn Tyr Phe Ile Leu Asp
            100                 105                 110

Ile Lys Lys Gly Ser Leu Thr Pro Leu Ala Gln Asp Gln Ala Gly Asp
        115                 120                 125

Ile Gln Tyr Ala Gln Trp Ser Pro Met Asn Asn Ser Ile Ala Tyr Val
    130                 135                 140

Arg Gly Asn Asp Leu Tyr Ile Trp Asn Asn Gly Lys Thr Lys Arg Ile
145                 150                 155                 160

Thr Glu Asn Gly Gly Pro Asp Ile Phe Asn Gly Val Pro Asp Trp Val
                165                 170                 175

Tyr Glu Glu Glu Ile Phe Gly Asp Arg Phe Ala Leu Trp Phe Ser Pro
            180                 185                 190

Asp Gly Glu Tyr Leu Ala Tyr Leu Arg Phe Asn Glu Thr Gly Val Pro
        195                 200                 205

Thr Tyr Thr Ile Pro Tyr Tyr Lys Asn Lys Gln Lys Ile Ala Pro Ala
    210                 215                 220

Tyr Pro Arg Glu Leu Glu Ile Arg Tyr Pro Lys Val Ser Ala Lys Asn
225                 230                 235                 240

Pro Thr Val Gln Phe His Leu Leu Asn Ile Ala Ser Ser Gln Glu Thr
                245                 250                 255

Thr Ile Pro Val Thr Ala Phe Pro Glu Asn Asp Leu Val Ile Gly Glu
            260                 265                 270

Val Ala Trp Leu Ser Ser Gly His Asp Ser Val Ala Tyr Arg Ala Phe
        275                 280                 285

Asn Arg Val Gln Asp Arg Glu Lys Ile Val Ser Val Lys Val Glu Ser
    290                 295                 300

Lys Glu Ser Lys Val Ile Arg Glu Arg Asp Gly Thr Asp Gly Trp Ile
305                 310                 315                 320

Asp Asn Leu Leu Ser Met Ser Tyr Ile Gly Asn Val Asn Gly Lys Glu
                325                 330                 335

Tyr Tyr Val Asp Ile Ser Asp Ala Ser Gly Trp Ala His Ile Tyr Leu
            340                 345                 350

Tyr Pro Val Asp Gly Gly Lys Glu Ile Ala Leu Thr Lys Gly Glu Trp
        355                 360                 365

Glu Val Val Ala Ile Leu Lys Val Asp Thr Lys Lys Lys Leu Ile Tyr
    370                 375                 380

Phe Thr Ser Thr Lys Tyr His Ser Thr Thr Arg His Val Tyr Ser Val
385                 390                 395                 400

Ser Tyr Asp Thr Lys Val Met Thr Pro Leu Val Asn Asp Lys Glu Ala
                405                 410                 415
```

-continued

Ala Tyr Tyr Thr Ala Ser Phe Ser Ala Lys Gly Gly Tyr Tyr Ile Leu
420 425 430

Ser Tyr Gln Gly Pro Asn Val Pro Tyr Gln Glu Leu Tyr Ser Thr Lys
435 440 445

Asp Ser Lys Lys Pro Leu Lys Thr Ile Thr Ser Asn Asp Ala Leu Leu
450 455 460

Glu Lys Leu Lys Glu Tyr Lys Leu Pro Lys Val Ser Phe Phe Glu Ile
465 470 475 480

Lys Leu Pro Ser Gly Glu Thr Leu Asn Val Lys Gln Arg Leu Pro Pro
485 490 495

Asn Phe Asn Pro His Lys Lys Tyr Pro Val Leu Phe Thr Pro Tyr Gly
500 505 510

Gly Pro Gly Ala Gln Glu Val Ser Gln Ala Trp Asn Ser Leu Asp Phe
515 520 525

Lys Ser Tyr Ile Thr Ser Asp Pro Glu Leu Glu Tyr Val Thr Trp Thr
530 535 540

Val Asp Asn Arg Gly Thr Gly Tyr Lys Gly Arg Lys Phe Arg Ser Ala
545 550 555 560

Val Ala Lys Arg Leu Gly Phe Leu Glu Ala Gln Asp Gln Val Phe Ala
565 570 575

Ala Lys Glu Val Leu Lys Asn Arg Trp Ala Asp Lys Asp His Ile Gly
580 585 590

Ile Trp Gly Trp Ser Tyr Gly Gly Phe Leu Thr Ala Lys Thr Leu Glu
595 600 605

Thr Asp Ser Gly Val Phe Thr Phe Gly Ile Ser Thr Ala Pro Val Ser
610 615 620

Asp Phe Arg Leu Tyr Asp Ser Met Tyr Thr Glu Arg Tyr Met Lys Thr
625 630 635 640

Val Glu Leu Asn Ala Asp Gly Tyr Ser Glu Thr Ala Val His Lys Val
645 650 655

Asp Gly Phe Lys Asn Leu Lys Gly His Tyr Leu Ile Gln His Gly Thr
660 665 670

Gly Asp Asp Asn Val His Phe Gln Asn Ala Ala Val Leu Ser Asn Thr
675 680 685

Leu Met Asn Gly Gly Val Thr Ala Asp Lys Leu Thr Thr Gln Trp Phe
690 695 700

Thr Asp Ser Asp His Gly Ile Arg Tyr Asp Met Asp Ser Thr Tyr Gln
705 710 715 720

Tyr Lys Gln Leu Ser Lys Met Val Tyr Asp Gln Lys Gln Arg Arg Pro
725 730 735

Glu Ser Pro Pro Met His Gln Trp Ser
740 745

<210> SEQ ID NO 4
<211> LENGTH: 451
<212> TYPE: PRT
<213> ORGANISM: Artificial Sequence
<220> FEATURE:
<223> OTHER INFORMATION: Leucine aminopeptidase

<400> SEQUENCE: 4

Glu Pro Phe Gly Trp Pro Phe Lys Pro Met Val Thr Gln Asp Asp Leu
1 5 10 15

Gln Asn Lys Ile Lys Leu Lys Asp Ile Met Ala Gly Val Glu Lys Leu
20 25 30

-continued

```
Gln Ser Phe Ser Asp Ala His Pro Glu Lys Asn Arg Val Phe Gly Gly
        35                  40                  45

Asn Gly His Lys Asp Thr Val Glu Trp Ile Tyr Asn Glu Ile Lys Ala
    50                  55                  60

Thr Gly Tyr Tyr Asp Val Lys Lys Gln Glu Gln Val His Leu Trp Ser
65                  70                  75                  80

His Ala Glu Ala Ala Leu Asn Ala Asn Gly Lys Asp Leu Lys Ala Ser
                85                  90                  95

Ala Met Ser Tyr Ser Pro Pro Ala Ser Lys Ile Met Ala Glu Leu Val
            100                 105                 110

Val Ala Lys Asn Asn Gly Cys Asn Ala Thr Asp Tyr Pro Ala Asn Thr
        115                 120                 125

Gln Gly Lys Ile Val Leu Val Glu Arg Gly Val Cys Ser Phe Gly Glu
    130                 135                 140

Lys Ser Ala Gln Ala Gly Asp Ala Lys Ala Ala Gly Ala Ile Val Tyr
145                 150                 155                 160

Asn Asn Val Pro Gly Ser Leu Ala Gly Thr Leu Gly Gly Leu Asp Lys
                165                 170                 175

Arg His Val Pro Thr Ala Gly Leu Ser Gln Glu Asp Gly Lys Asn Leu
            180                 185                 190

Ala Thr Leu Val Ala Ser Gly Lys Ile Asp Val Thr Met Asn Val Ile
        195                 200                 205

Ser Leu Phe Glu Asn Arg Thr Thr Trp Asn Val Ile Ala Glu Thr Lys
    210                 215                 220

Gly Gly Asp His Asn Asn Val Ile Met Leu Gly Ala His Ser Asp Ser
225                 230                 235                 240

Val Asp Ala Gly Pro Gly Ile Asn Asp Asn Gly Ser Gly Ser Ile Gly
                245                 250                 255

Ile Met Thr Val Ala Lys Ala Leu Thr Asn Phe Lys Leu Asn Asn Ala
            260                 265                 270

Val Arg Phe Ala Trp Trp Thr Ala Glu Glu Phe Gly Leu Leu Gly Ser
        275                 280                 285

Thr Phe Tyr Val Asn Ser Leu Asp Asp Arg Glu Leu His Lys Val Lys
    290                 295                 300

Leu Tyr Leu Asn Phe Asp Met Ile Gly Ser Pro Asn Phe Ala Asn Gln
305                 310                 315                 320

Ile Tyr Asp Gly Asp Gly Ser Ala Tyr Asn Met Thr Gly Pro Ala Gly
                325                 330                 335

Ser Ala Glu Ile Glu Tyr Leu Phe Glu Lys Phe Phe Asp Asp Gln Gly
            340                 345                 350

Ile Pro His Gln Pro Thr Ala Phe Thr Gly Arg Ser Asp Tyr Ser Ala
        355                 360                 365

Phe Ile Lys Arg Asn Val Pro Ala Gly Gly Leu Phe Thr Gly Ala Glu
    370                 375                 380

Val Val Lys Thr Pro Glu Gln Val Lys Leu Phe Gly Gly Glu Ala Gly
385                 390                 395                 400

Val Ala Tyr Asp Lys Asn Tyr His Arg Lys Gly Asp Thr Val Ala Asn
                405                 410                 415

Ile Asn Lys Gly Ala Ile Phe Leu Asn Thr Arg Ala Ile Ala Tyr Ala
            420                 425                 430

Ile Ala Glu Tyr Ala Arg Ser Leu Lys Gly Phe Pro Thr Arg Pro Lys
        435                 440                 445

Thr Gly Lys
```

450

<210> SEQ ID NO 5
<211> LENGTH: 7
<212> TYPE: PRT
<213> ORGANISM: Artificial Sequence
<220> FEATURE:
<223> OTHER INFORMATION: Peptide

<400> SEQUENCE: 5

Pro Gln Pro Gln Pro Phe Pro
1 5

<210> SEQ ID NO 6
<211> LENGTH: 5
<212> TYPE: PRT
<213> ORGANISM: Artificial Sequence
<220> FEATURE:
<223> OTHER INFORMATION: Peptide

<400> SEQUENCE: 6

Pro Gln Gln Pro Tyr
1 5

<210> SEQ ID NO 7
<211> LENGTH: 33
<212> TYPE: PRT
<213> ORGANISM: Artificial Sequence
<220> FEATURE:
<223> OTHER INFORMATION: Peptide

<400> SEQUENCE: 7

Leu Gln Leu Gln Pro Phe Pro Gln Pro Gln Leu Pro Tyr Pro Gln Pro
1 5 10 15

Gln Leu Pro Tyr Pro Gln Pro Gln Leu Pro Tyr Pro Gln Pro Gln Pro
20 25 30

Phe

<210> SEQ ID NO 8
<211> LENGTH: 32
<212> TYPE: PRT
<213> ORGANISM: Artificial Sequence
<220> FEATURE:
<223> OTHER INFORMATION: peptide

<400> SEQUENCE: 8

Gln Leu Gln Pro Phe Pro Gln Pro Gln Leu Pro Tyr Pro Gln Pro Gln
1 5 10 15

Leu Pro Tyr Pro Gln Pro Gln Leu Pro Tyr Pro Gln Pro Gln Pro Phe
20 25 30

<210> SEQ ID NO 9
<211> LENGTH: 31
<212> TYPE: PRT
<213> ORGANISM: Artificial Sequence
<220> FEATURE:
<223> OTHER INFORMATION: peptide

<400> SEQUENCE: 9

Leu Gln Pro Phe Pro Gln Pro Gln Leu Pro Tyr Pro Gln Pro Gln Leu
1 5 10 15

Pro Tyr Pro Gln Pro Gln Leu Pro Tyr Pro Gln Pro Gln Pro Phe
20 25 30

<210> SEQ ID NO 10
<211> LENGTH: 30
<212> TYPE: PRT
<213> ORGANISM: Artificial Sequence
<220> FEATURE:
<223> OTHER INFORMATION: peptide

<400> SEQUENCE: 10

```
Gln Pro Phe Pro Gln Pro Gln Leu Pro Tyr Pro Gln Pro Gln Leu Pro
1               5                   10                  15

Tyr Pro Gln Pro Gln Leu Pro Tyr Pro Gln Pro Gln Pro Phe
            20                  25                  30
```

<210> SEQ ID NO 11
<211> LENGTH: 28
<212> TYPE: PRT
<213> ORGANISM: Artificial Sequence
<220> FEATURE:
<223> OTHER INFORMATION: peptide

<400> SEQUENCE: 11

```
Phe Pro Gln Pro Gln Leu Pro Tyr Pro Gln Pro Gln Leu Pro Tyr Pro
1               5                   10                  15

Gln Pro Gln Leu Pro Tyr Pro Gln Pro Gln Pro Phe
            20                  25
```

<210> SEQ ID NO 12
<211> LENGTH: 26
<212> TYPE: PRT
<213> ORGANISM: Artificial Sequence
<220> FEATURE:
<223> OTHER INFORMATION: peptide

<400> SEQUENCE: 12

```
Gln Pro Gln Leu Pro Tyr Pro Gln Pro Gln Leu Pro Tyr Pro Gln Pro
1               5                   10                  15

Gln Leu Pro Tyr Pro Gln Pro Gln Pro Phe
            20                  25
```

<210> SEQ ID NO 13
<211> LENGTH: 24
<212> TYPE: PRT
<213> ORGANISM: Artificial Sequence
<220> FEATURE:
<223> OTHER INFORMATION: peptide

<400> SEQUENCE: 13

```
Gln Leu Pro Tyr Pro Gln Pro Gln Leu Pro Tyr Pro Gln Pro Gln Leu
1               5                   10                  15

Pro Tyr Pro Gln Pro Gln Pro Phe
            20
```

<210> SEQ ID NO 14
<211> LENGTH: 23
<212> TYPE: PRT
<213> ORGANISM: Artificial Sequence
<220> FEATURE:
<223> OTHER INFORMATION: peptide

<400> SEQUENCE: 14

```
Leu Pro Tyr Pro Gln Pro Gln Leu Pro Tyr Pro Gln Pro Gln Leu Pro
1               5                   10                  15

Tyr Pro Gln Pro Gln Pro Phe
            20
```

<210> SEQ ID NO 15
<211> LENGTH: 21
<212> TYPE: PRT
<213> ORGANISM: Artificial Sequence
<220> FEATURE:
<223> OTHER INFORMATION: peptide

<400> SEQUENCE: 15

Tyr Pro Gln Pro Gln Leu Pro Tyr Pro Gln Pro Gln Leu Pro Tyr Pro
1 5 10 15

Gln Pro Gln Pro Phe
20

<210> SEQ ID NO 16
<211> LENGTH: 19
<212> TYPE: PRT
<213> ORGANISM: Artificial Sequence
<220> FEATURE:
<223> OTHER INFORMATION: peptide

<400> SEQUENCE: 16

Gln Pro Gln Leu Pro Tyr Pro Gln Pro Gln Leu Pro Tyr Pro Gln Pro
1 5 10 15

Gln Pro Phe

<210> SEQ ID NO 17
<211> LENGTH: 17
<212> TYPE: PRT
<213> ORGANISM: Artificial Sequence
<220> FEATURE:
<223> OTHER INFORMATION: peptide

<400> SEQUENCE: 17

Gln Leu Pro Tyr Pro Gln Pro Gln Leu Pro Tyr Pro Gln Pro Gln Pro
1 5 10 15

Phe

<210> SEQ ID NO 18
<211> LENGTH: 16
<212> TYPE: PRT
<213> ORGANISM: Artificial Sequence
<220> FEATURE:
<223> OTHER INFORMATION: peptide

<400> SEQUENCE: 18

Leu Pro Tyr Pro Gln Pro Gln Leu Pro Tyr Pro Gln Pro Gln Pro Phe
1 5 10 15

<210> SEQ ID NO 19
<211> LENGTH: 14
<212> TYPE: PRT
<213> ORGANISM: Artificial Sequence
<220> FEATURE:
<223> OTHER INFORMATION: peptide

<400> SEQUENCE: 19

Tyr Pro Gln Pro Gln Leu Pro Tyr Pro Gln Pro Gln Pro Phe
1 5 10

<210> SEQ ID NO 20
<211> LENGTH: 12
<212> TYPE: PRT
<213> ORGANISM: Artificial Sequence
<220> FEATURE:
<223> OTHER INFORMATION: peptide

<400> SEQUENCE: 20

Gln Pro Gln Leu Pro Tyr Pro Gln Pro Gln Pro Phe
1 5 10

<210> SEQ ID NO 21
<211> LENGTH: 10
<212> TYPE: PRT
<213> ORGANISM: Artificial Sequence
<220> FEATURE:
<223> OTHER INFORMATION: peptide

<400> SEQUENCE: 21

Gln Leu Pro Tyr Pro Gln Pro Gln Pro Phe
1 5 10

<210> SEQ ID NO 22
<211> LENGTH: 9
<212> TYPE: PRT
<213> ORGANISM: Artificial Sequence
<220> FEATURE:
<223> OTHER INFORMATION: peptide

<400> SEQUENCE: 22

Leu Pro Tyr Pro Gln Pro Gln Pro Phe
1 5

<210> SEQ ID NO 23
<211> LENGTH: 7
<212> TYPE: PRT
<213> ORGANISM: Artificial Sequence
<220> FEATURE:
<223> OTHER INFORMATION: peptide

<400> SEQUENCE: 23

Tyr Pro Gln Pro Gln Pro Phe
1 5

<210> SEQ ID NO 24
<211> LENGTH: 5
<212> TYPE: PRT
<213> ORGANISM: Artificial Sequence
<220> FEATURE:
<223> OTHER INFORMATION: peptide

<400> SEQUENCE: 24

Gln Pro Gln Pro Phe
1 5

<210> SEQ ID NO 25
<211> LENGTH: 3
<212> TYPE: PRT
<213> ORGANISM: Artificial Sequence
<220> FEATURE:
<223> OTHER INFORMATION: peptide

<400> SEQUENCE: 25

Gln Pro Phe
1